United States Patent

Hayashi et al.

[11] 3,966,792
[45] June 29, 1976

[54] PROSTAGLANDIN COMPOUNDS

[75] Inventors: Masaki Hayashi; Seiji Kori, both of Takatsuki; Isao Ohyama, Kyoto; Hirofumi Endo, Fujinomiya, all of Japan

[73] Assignee: Ono Pharmaceutical Co., Ltd., Osaka, Japan

[22] Filed: Feb. 27, 1974

[21] Appl. No.: 446,241

[30] Foreign Application Priority Data
Feb. 28, 1973  Japan.............................. 48-23068

[52] U.S. Cl................... 260/468 D; 260/210 R; 260/246 R; 260/343.3 R; 260/345.7; 260/346.2 R; 260/347.3; 260/408 R; 260/501.1; 260/501.17; 260/514 D; 260/617 R; 424/305; 424/317
[51] Int. Cl.².................. C07C 61/38; C07C 69/74
[58] Field of Search.................. 260/468 D, 514 D

[56] References Cited
UNITED STATES PATENTS
3,843,713  10/1974  Finch et al........................ 260/468
FOREIGN PATENTS OR APPLICATIONS
782,822   8/1972  Belgium........................... 260/468
7,301,094 7/1973  Netherlands...................... 260/468

*Primary Examiner*—Robert Gersil
*Attorney, Agent, or Firm*—Albert H. Graddis; Frank S. Chow

[57] ABSTRACT

New prostaglandin analogues having therapeutic utility of the formula:

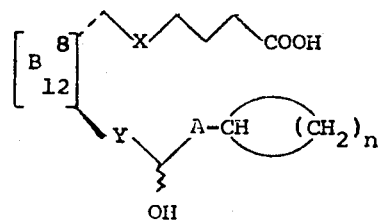

(wherein B is a grouping of the formula:

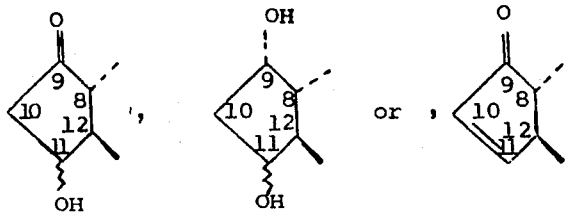

X is $-CH_2CH_2-$ or cis $-CH=CH-$, Y is trans $-CH=CH-$ or, when X is $=CH_2CH_2-$, Y is additionally $-CH_2CH_2-$, A is alkyl of 1 through 3 carbon atoms, $n$ is 4 or 5, and $\sim$ indicates attachment of the hydroxy radical to the carbon atom in alpha or beta configuration), and alkyl esters thereof, and cyclodextrin clathrates of such acids and esters, and non-toxic salts of such acids.

9 Claims, No Drawings

PROSTAGLANDIN COMPOUNDS

This invention relates to new prostaglandin analogues, to a process for their preparation and to pharmaceutical compositions containing them.

Prostaglandins are derivatives of prostanoic acid which has the following formula:

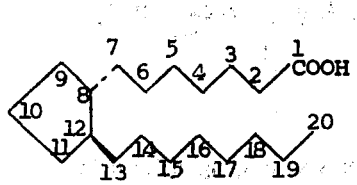

Various types of prostaglandins are known, the types depending inter alia on the structure and substituents on the alicyclic ring. For example, the alicyclic rings of prostaglandins E(PGE), F(PGF) and A(PGA) have the structures:

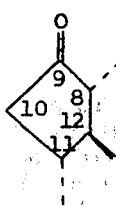 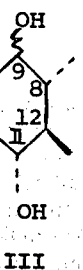 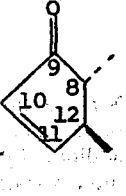

II   III   IV respectively.

Such compounds are sub-classified according to the position of double bond(s) in the side chain(s) attached to the 8- and 12-positions of the alicyclic ring. Thus PG-1 compounds have a trans-double bond between $C_{13}-C_{14}$(trans-$\Delta^{13}$), PG-2 compounds have a cis-double bond between $C_5-C_6$ and a trans-double bond between $C_{13}-C_{14}$(cis-$\Delta^5$, trans-$\Delta^{13}$), and PG-3 compounds have cis-double bonds between $C_5-C_6$ and $C_{17}-C_{18}$ and a trans-double bond between $C_{13}-C_{14}$(cis-$\Delta^5$, trans-$\Delta^{13}$, cis-$\Delta^{17}$). For example, prostaglandin $F_{1\alpha}$ (PGF$_{1\alpha}$) and prostaglandin $E_1$ (PGE$_1$) are characterized by the following structures V and VI.

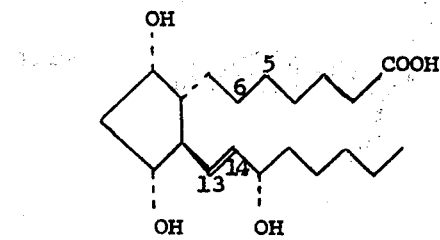

and

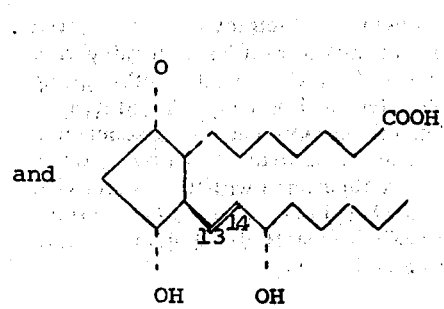

respectively. The structures of PGF$_2\alpha$ and PGE$_2$, as members of the PG-2 group, correspond to those of formulae V and VI respectively with a cis-double bond between the carbon atoms in positions 5 and 6. Compounds in which the double bond between the carbon atoms in positions 13 and 14 of members of the PG-1 group is replaced by ethylene(—CH$_2$CH$_2$—) are known as dihydro-prostaglandins, e.g. dihydro-prostaglandin-$F_{1\alpha}$ (dihydro-PGF$_{1\alpha}$) and dihydro-prostaglandin-E$_1$ (dihydro-PGE$_1$).

Moreover, when one or more methylene groups are eliminated from the aliphatic group attached to the 12-position of the alicyclic ring of the prostaglandins the compounds are known, in accordance with the usual rules of organic nomenclature, as $\omega$-nor-prostaglandins and, when more than one methylene group is eliminated, the number is indicated by di-, tri- etc. before the prefix "nor."

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyper-lipemia. PGE$_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found that by eliminating a plurality of methylene groups from the aliphatic group attached to the 12-position of the alicyclic ring of prostaglandins E, F and A and substituting a cyclopentyl or cyclohexyl group on the modified aliphatic group, new analogues of the fundamental prostaglandins are obtained which possess the pharmacological properties of 'natural' prostaglandins and are, in some aspects of their activities, an improvement, for example they possess an enhanced strength of activity or a prolonged duration of activity.

The present invention accordingly provides new prostaglandin analogues of the general formula:

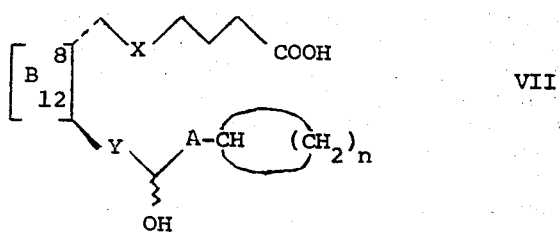

(wherein B represents a grouping of formula IV as indicated above or a grouping of the formula:

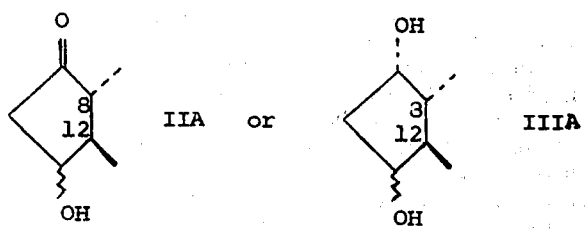

, X represents —CH$_2$CH$_2$— or cis—CH=CH—, Y represents trans —CH=CH— or, when X is —CH$_2$CH$_2$—, Y may additionally represent —CH$_2$CH$_2$—, A represents a straight- or branched-chain alkyl radical containing from 1 to 3 carbon atoms (preferably —CH(CH$_3$)— or —CH$_2$CH$_2$—), n represents 4 or 5, and ∿ indicates attachment of the hydroxy radical to the carbon atom in alpha or beta configuration), and alkyl esters thereof having from 1 to 12 carbon atoms in a straight- or branched-chain, and cyclodextrin clathrates of such acids and esters, and non-toxic (e.g. sodium) salts of the acids of formula VII.

The present invention is concerned with all compounds of general formula VII in the 'natural' form or its enatiomeric form, or mixtures thereof, more particularly the racemic form consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms in the positions identified as 8 and 12 and at the C-15 carbon atom which has attached to it a hydroxy radical. Still further centres of chirality occur when the alicyclic group B carries a hydroxy radical on the carbon atom in position 11 (i.e. when the ring is that of formula IIA) or hydroxy radicals in positions 9 and 11 (i.e. when the ring is that of formula IIIA). The presence of chirality leads, as is well known, to the existence of isomerism. However, the compounds of general formula VII all have such a configuration that the side chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans configuration and have a hydroxy radical in the 15-position are to be considered within the scope of general formula VII.

A preferred embodiment of the present invention comprises compounds of the formula:

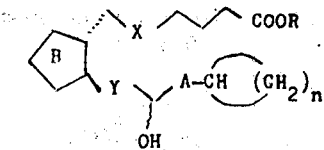

wherein B represents a grouping of formula:

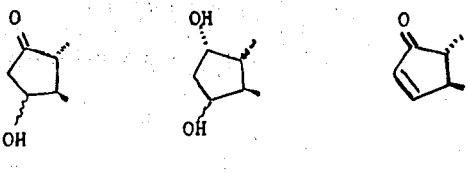

X represents —CH$_2$CH$_2$— or cis—CH=CH—, Y represents trans—CH=CH— or, when X is —CH$_2$CH$_2$—, additionally —CH$_2$CH$_2$—, A represents a straight- or branched-chain alkyl radical containing from one to 3 carbon atoms, n represents an integer of 4 or, when A is a branched-chain alkyl radical, additionally an integer of 5, and R represents a straight- or branched-chain alkyl radical containing from one to 12 carbon atoms and the corresponding PG-alcohols, and cyolodextrin clathrates of the said acids, esters and alcohols, and the non-toxic salts of the acids.

According to a feature of the present invention, the prostaglandin compounds of general formula VII are prepared by the process which comprises reacting a bicyclo-octane derivative of the general formula:

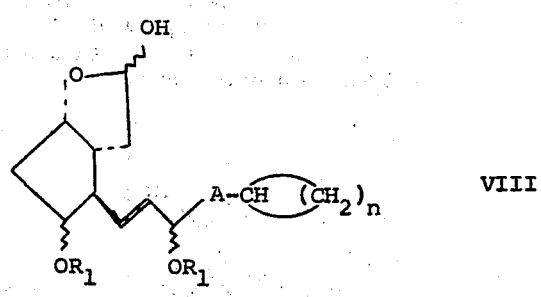

(wherein R$_1$ represents a 2-tetrahydropyranyl group unsubstituted or substituted by at least one alkyl radical, or a 2-tetrahydrofuranyl or 1-ethoxyethyl group, and is preferably 2-tetrahydropyranyl, A and n are as hereinbefore defined, and ∿ indicates attachment of the OR$_1$ and hydroxy groups to the carbon atom in alpha or beta configuration) with 4-carboxy-n-butylidenetriphenylphosphorane of the formula (C$_6$H$_5$)$_3$P=CH.CH$_2$CH$_2$CH$_2$COOH to obtain a compound of the general formula:

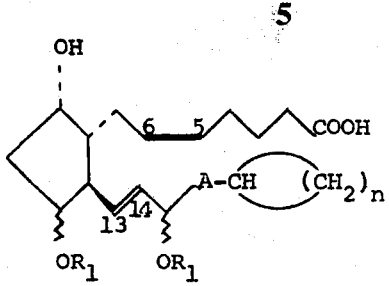

(wherein A, n, $R_1$ and  have the meanings hereinbefore specified), optionally hydrogenating the cis-double bond between $C_5-C_6$ and the trans-double bond between $C_{13}-C_{14}$ of the compounds of general formula IX, and/or optionally converting by methods known per se the 9α-hydroxy radical in the compounds of general formula IX, or their hydrogenated derivatives, to an oxo group, and hydrolyzing the tetrahydropyranyloxy, tetrahydrofuranyloxy or ethoxyethoxy group in the resulting prostaglandin compound, all conforming to the general formula:

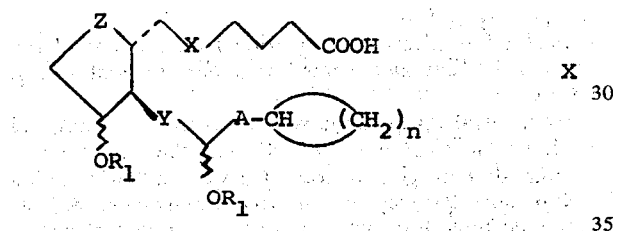

(wherein Z represents

or C=O, and X, Y, A, n, $R_1$ and ⌇ have the meanings hereinbefore specified) to hydroxy radicals to obtain a PGF or PGE compound of the general formula:

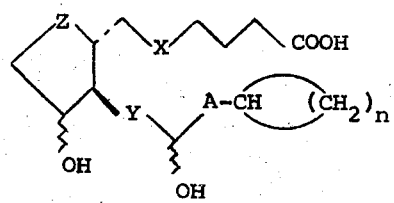

(wherein the various symbols and ⌇ have the meanings hereinbefore specified) and, if desired, converting by methods known per se the PGE alicyclic ring (Z represents C=O) into that of a PGA compound. By the term "methods known per se" as used in this specification is meant methods heretofore used or described in the chemical literature.

The intermediate compounds of general formula X, which embraces compounds of formula IX, are new compounds and as such constitute a feature of the invention. The intermediates of formula IX may thus be converted into the prostaglandin analogues of general formula VII by the reactions depicted schematically below:

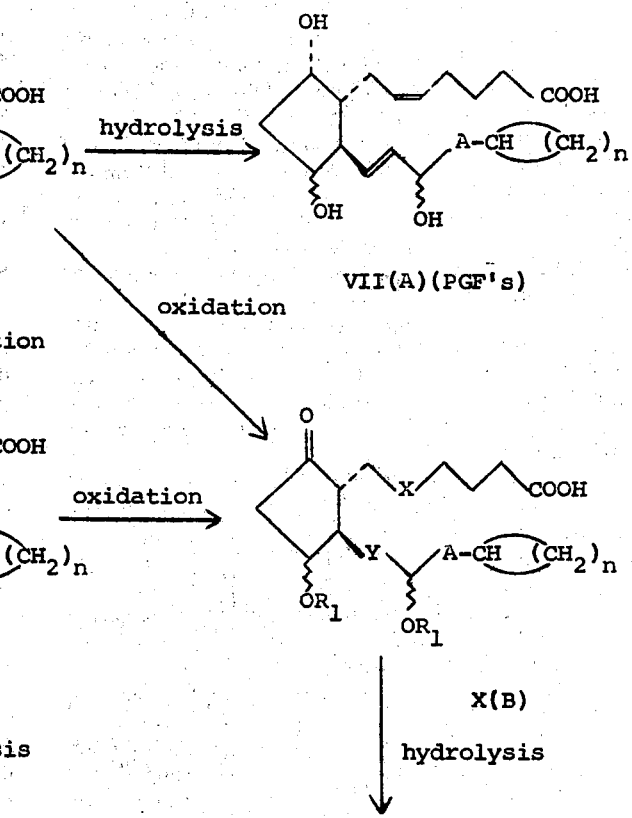
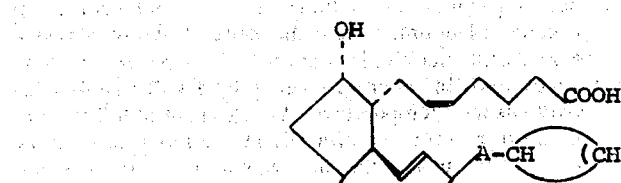

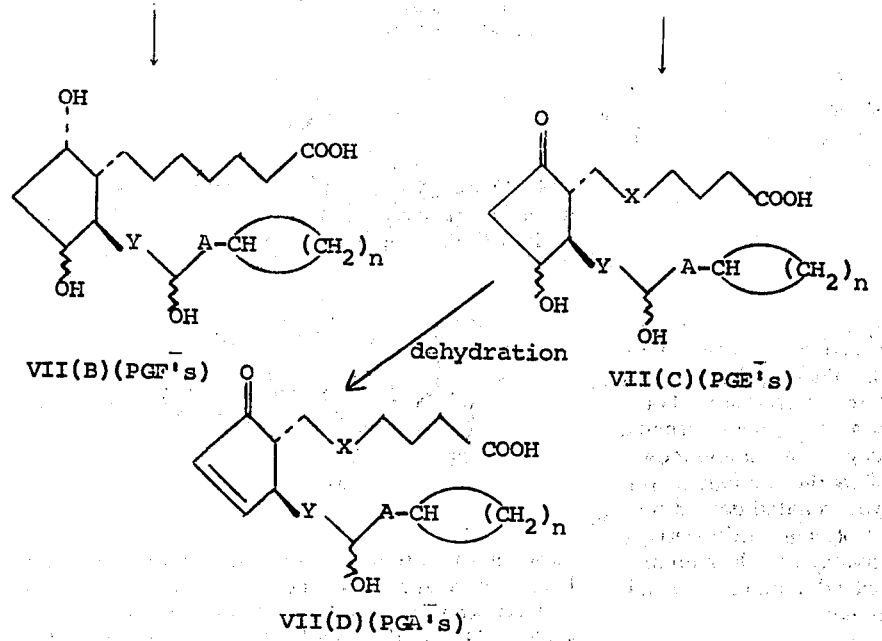

wherein the various symbols and $\mathcal{M}$ are as hereinbefore defined.

Catalytic hydrogenation of the cyclopentane compounds of general formula IX can be carried out as follows:

The hydrogenation catalyst, i.e., a catalyst usually used for the hydrogenation of double bonds such as various forms of platinum, palladium or nickel, is suspended in an adequate amount of a solvent acting as reaction medium, and the suspension placed in an apparatus appropriate for a catalytic reduction process. The air inside the apparatus is replaced by hydrogen, and a solution of the cyclopentane compound in a suitable inert solvent (for example methanol, ethanol, water, dioxan or acetic acid, or a mixture of two or more of them) is added to the suspension of the catalyst. The reaction takes place at about 0°C. to 50°C. until one or two times the molar quantity of hydrogen has been consumed according to whether or not it is desired to reduce the trans $C_{13}$–$C_{14}$ double bond in the starting material of formula IX as well as the cis $C_5$–$C_6$ double bond, for example for a period of 0.5 to 8 hours. After completion of the reaction, the catalyst is removed by means of a filter, and the filtrate concentrated. If necessary, the residue is purified by chromatography using silica gel or silica gel impregnated with silver nitrate.

The $C_{13}$–$C_{14}$ double bond is difficult to hydrogenate due to steric hindrance by the tetrahydropyranyloxy, tetrahydrofuranyloxy or ethoxyethoxy group $OR_1$; however, use of platinum oxide as catalyst is satisfactory for the purpose. Hydrogenation of the $C_5$–$C_6$ double bond only can be effected by appropriate selection of the catalyst (5 percent palladium on carbon is satisfactory), the reaction temperature and time.

The PGF alicyclic ring in the compounds of general formulae IX and X [including X(A)] can be converted into a PGE ring [cf. formula X(B)] by methods known per se for the conversion of a hydroxy group in the 9-position of a prostaglandin to an oxo radical, for example by means of a chromic acid solution (e.g. obtained from chromium trioxide, manganese sulphate, sulphuric acid and water) or Jones' reagent [cf. J. Chem. Soc., 39 (1946)].

The tetrahydropyranyloxy, tetrahydrofuranyloxy and ethoxyethoxy groups ($\mathcal{M}OR_1$) in the intermediate compounds of general formulae IX and X [including X(A) and (B)] may be converted into hydroxy radicals by mild hydrolysis with an aqueous solution of an organic acid, e.g. acetic acid, or with a dilute inorganic acid, e.g. dilute hydrochloric acid. Advantageously an organic solvent miscible with water, such as tetrahydrofuran or an alcohol, is employed. The treatment of the compounds of general formulae IX and X may be carried out at a temperature ranging from ambient temperature to 60°C. (preferably at a temperature below 45°C.) with an acid mixture, such as a mixture of acetic acid, water and tetrahydrofuran, or a mixture of hydrochloric acid with tetrahydrofuran or methanol.

The PGE compounds of general formula XI [Z represents C=O, cf. formula VII(C)] can be converted into corresponding PGA compounds by methods known per se [cf. Proceedings of Nobel Symposium, Vol. II, 162–3 (1967)], for example by subjecting the PGE's to dehydration using an aqueous solution of an organic or inorganic acid having a higher concentration than that employed for hydrolysis of compounds of general formulae IX and X (e.g. acetic acid or 1N hydrochloric acid, optionally in the presence of cupric chloride dihydrate when hydrochloric acid is employed), and heating at a temperature of 30°–60°C.

The reaction between the bicyclo-octane derivatives of general formula VIII and 4-carboxy-n-butylidenetriphenylphosphorane [obtained by the reaction of sodiomethylsulphinylcarbanide with 4-carboxy-n-butyltriphenylphosphonium bromide] is carried out under the normal conditions utilized for effecting the Wittig reaction, e.g. in an inert solvent at or about ambient temperature. The reaction is preferably carried out in dimethylsulphoxide because the phosphorane compound is practically insoluble in other solvents, e.g. tetrahydrofuran, and because a cis-double bond must be formed stereospecifically in the Wittig reaction. For the better performance of the Wittig reaction more than two molecular equivalents of the phosphorane compound are required for each mole of the bicyclo-octane reactant. The reaction is generally effected at a temperature of 0°–40°C., preferably at 20°–30°C., and is usually complete after about 1 to 5 hours at laboratory temperature. The acid product of formula IX may be extracted from the reaction mixture by conventional procedures and further purified by column chromatography in silica gel.

The bicyclo-octane derivative of general formula VIII employed as starting materials in the process of the invention can be prepared by the reaction sequence schematically depicted below:

The bicyclo-octane compound of formula XII wherein $R_2$ is an acetyl group, viz. 2-oxa-3-oxo-6-syn-formyl-7-anti-acetoxy-cis-bicyclo[3,3,0]octane, is a known compound [E. J. Corey et al, J. Amer. Chem. Soc. 92, 397 (1970)]. A compound of formula XII wherein $R_2$ is p-phenylbenzoyl, viz. 2-oxa-3-oxo-6-syn-formyl-7-anti-(p-phenylbenzoyloxy)-cis-bicyclo[3,3,-0]octane, is a known compound [N. M. Weinshenker et al, Tetrahedron Letters, 3285–3288 (1972)]. A compound of formula XII wherein -$OR_2$ is β-acetoxy can be prepared by the method described in Tetrahedrom Letters, 3265–3268 (1972). The other compounds of that formula, i.e. $R_2$ is benzoyl, can be obtained from the known compounds by application of known procedures.

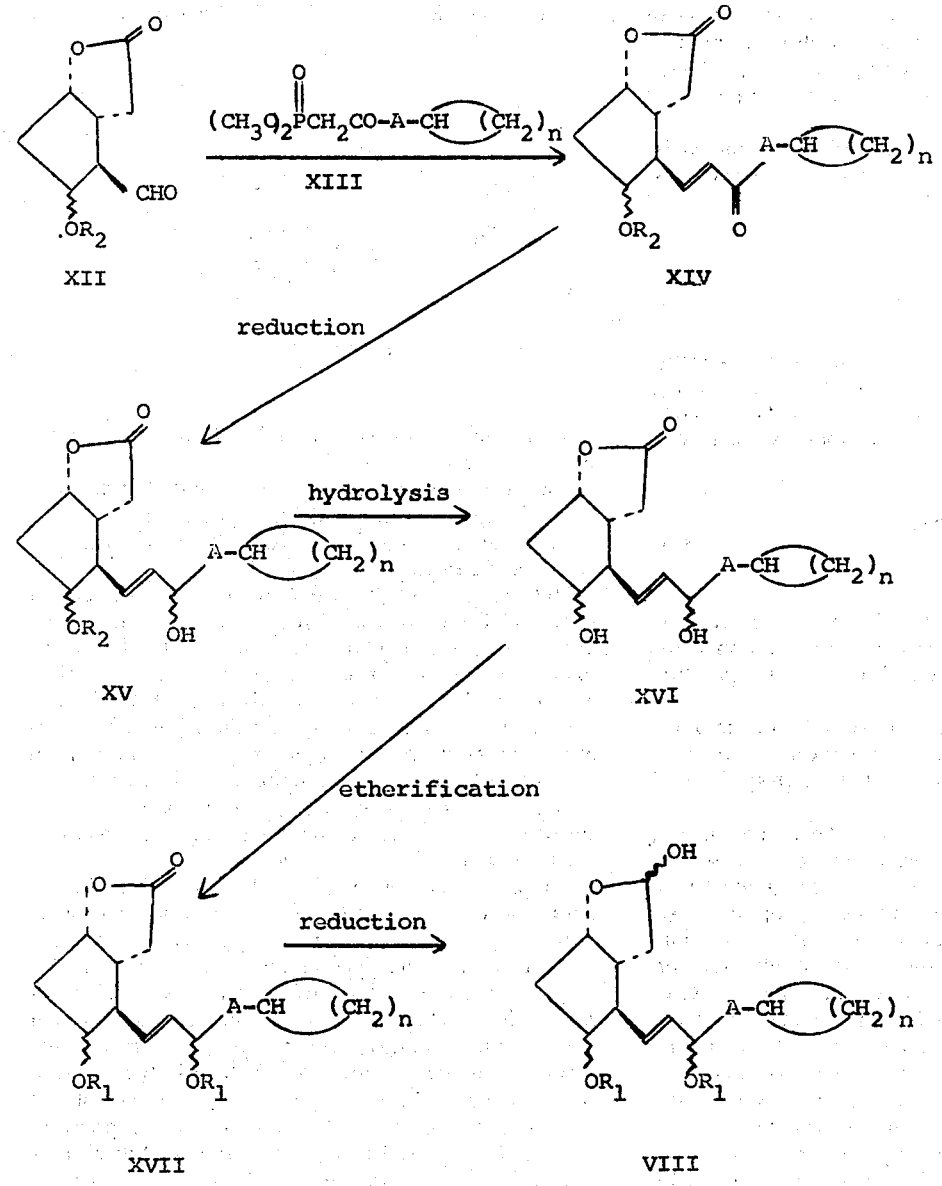

wherein $R_2$ represents an acetyl, p-phenylbenzoyl or benzoyl group, and A, $R_1$, n and ⌇ are as hereinbefore specified.

The phosphonates of formula XIII are initially converted to corresponding ylides by reaction with sodium hydride or lithium hydride in tetrahydrofuran, and the bicyclo-octane compound in solution in tetrahydrofuran is added to the ylide solution, and the ensuing Wittig reaction carried out at or about ambient temperature, yields stereospecifically compounds of formula XIV with a trans double bond. Those compounds are reduced with zinc borohydride in dimethoxyethane or sodium borohydride in methanol to give compounds of formula XV, the α- and β-hydroxy isomers of which can, if desired, be separated by column chromatography. Hydrolysis of compounds of formula XV with, for example, an equimolar amount of anhydrous potassium carbonate in methanol at ambient temperature gives the diols of formula XVI, which are then etherified to introduce groups $R_1$ ($R_1$ being as hereinbefore defined), for example by reaction with the dihydropyran (or vinyl ethyl ether or dihydrofuran) in methylene chloride at ambient temperature using p-toluenesulphonic acid as a catalyst. Reduction of the ethers of formula XVII is then effected with diisobutylaluminium hydride in toluene at a low temperature, e.g. −60°C., and for 15–30 minutes to give the starting materials of formula VIII.

The phosphonates of formula XIII are obtained by forming the lithio derivative of dimethyl methylphosphonate

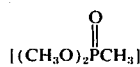

by treatment of the compound in solution in tetrahydrofuran with butyllithium at a low temperature (e.g. −15°C. to −65°C.), and reacting the lithiated compound with an alkyl cycloalkyl-alkanoate of the general formula:

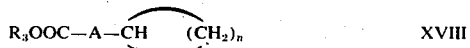            XVIII (wherein $R_3$ represents a straight- or branched-chain alkyl radical containing from 1 to 4 carbon atoms, and A and n are as hereinbefore defined) at a temperature at or below 0°C.

The prostaglandins of general formula VII obtained by the process of the present invention can be converted into salts or alkyl esters having from 1 to 12 carbon atoms in the alkyl moiety.

The salts may be prepared from the compounds of general formula VII by methods known per se, for example by reaction of stoichiometric quantities of acids of general formula VII and the appropriate base, e.g. an alkali metal hydroxide or carbonate, ammonium hydroxide, ammonia or an amine, in a suitable solvent. The salts may be isolated by concentration of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VII are not vitiated by sideeffects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of amonia by groups, which may be the same or different when more than one hydrogen atom is replaced, selected from, for example, alkyl groups containing from 1 to 6 carbon atoms and hydroxyalkyl groups containing from 1 to 3 carbon atoms.

Alkyl esters of the prostaglandins of general formula VII can be obtained by reaction of the acids with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our Belgian Pat. Nos. 775106 and 776294).

The prostaglandins of general formula VII can also be converted into prostaglandin alcohols, i.e. compounds in which the carboxy radical is replaced by the hydroxymethylene (i.e. —CH$_2$OH) group, of the general formula:

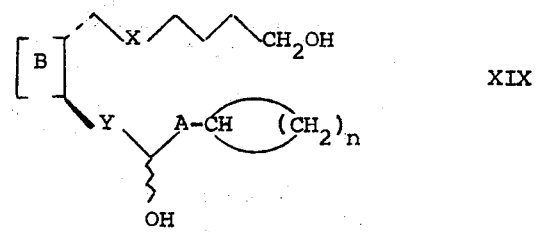            XIX wherein the various symbols and have the meanings hereinbefore specified.

The prostaglandin alcohols of general formula XIX can be prepared from the acids of general formula VII by application of the method described by Pike, Lincoln and Schneider in J. Org. Chem. 34, 3552–3557 (1969), for example by converting the acids of general formula VII into their methyl esters and then the esters into oximes, and reducing the oximes with lithium aluminium hydride to form oxime alcohols, and hydrolyzing then with, for example, acetic acid. PGF alcohols can also be obtained directly by reducing methyl esters of PGF compounds of general formula VII with lithium aluminium hydride. The alcohol derivatives of prostaglandins of general formula XIX possess pharmacological properties similar to the acids of general formula VII from which they are derived.

The prostaglandins of general formula VII and alkyl esters thereof, and corresponding alcohols of general formula XIX may, if desired, by converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70°C. during the preparation of the cyclodextrin clathrates. α, β or γ-Cyclodextrins or mixtures thereof may be used in the preparation of the cyclodextrin clathrates. Conversion into their cyclodextrin clathrates serves to increase the stability of the prostaglandin compounds.

The prostaglandin compounds of the present invention and their cyclodextrin clathrates and non-toxic salts, possess the valuable pharmacological properties typical of prostaglandins in a selective fashion including, in particular, hypotensive activity, inhibitory activity on blood platelet aggregation, inhibitory activity on gastric acid secretion and gastric ulceration, bronchodilator activity, luteolytic activity and stimulatory activity on uterine contraction and are useful in the treatment of hypertension, in the treatment of disorders of the peripheral circulation, in the prevention and treatment of cerebral thrombosis and myocardial infarction, in the treatment of gastric ulceration, in the treatment of asthma, in the control of oestrus in female mammals, in the prevention of pregnancy in female mammals and in the induction of labour in pregnant female mammals. In particular, 16-cyclohexyl-$\omega$-trinor-$PGE_2$, 16-cyclohexyl-$\omega$-trinor-$PGE_1$, 16-cyclohexyl-$\omega$-trinor-$PGE_1$ methyl ester, 16-cyclohexyl-$\omega$-trinor-$PGE_1$ isobutyl ester and 16-cyclohexyl-$\omega$-trinor-$PGE_1$ decyl ester are of value in the treatment of hypertension; 16-cyclohexyl-$\omega$-trinor-$PGE_1$ decyl ester, 16-cyclohexyl-$\omega$-trinor-$PGE_1$, 16-cyclohexyl-$\omega$-trinor-$PGE_1$ methyl ester and 16-cyclohexyl-$\omega$-trinor-$PGE_1$ isobutyl ester are of value in the treatment of disorders of the peripheral circulation and in the prevention and treatment of cerebral thrombosis and myocardial infarction; 16-cyclohexyl-$\omega$-trinor-$PGE_2$ and 16-cyclohexyl-$\omega$-trinor-$PGE_1$ are of value in the treatment of gastric ulceration, 16-cyclohexyl-$\omega$-trinor-$PGE_1$ decyl ester, 16-cyclohexyl-$\omega$-trinor-$PGE_1$ methyl ester, 16-cyclohexyl-$\omega$-trinor-$PGE_1$ isobutyl ester, 16-cyclopentyl-$\omega$-trinor-$PGE_2$ and 16-cyclopentyl-$\omega$-trinor-15-epi-$PGE_2$ are of value in the treatment of asthma; 16-cyclohexyl-$\omega$-trinor-$PGF_{2\alpha}$ and 16-cyclopentyl-$\omega$-trinor-$PGF_{2\alpha}$ are of value in the control of oestrus and the prevention of pregnancy in female mammals and 16-cyclohexyl-$\omega$-trinor-$PGF_{2\alpha}$ is of value in the induction of labour in pregnant female mammals. For example, in laboratory screening tests, (i) when administered intravenously to the allobarbitalanaesthetized dog, 16-cyclohexyl-$\omega$-trinor-$PGE_2$ produces falls in blood pressure of 38 mm.Hg and 72 mm.Hg lasting 25 minutes and 36 minutes respectively at doses of 0.2 and 0.5$\mu$g./kg. animal body weight respectively, 16-cyclohexyl-$\omega$-trinor-$PGE_1$ produces falls in blood pressure of 28 mm.Hg, 34 mm.Hg and 58 mm.Hg lasting 30 minutes, 36 minutes and 60 minutes respectively at doses of 0.1, 0.2 and 0.5$\mu$g./kg. animal body weight respectively, 16-cyclohexyl-$\omega$-trinor-$PGA_2$ produces falls in blood pressure of 20 mm.Hg and 30 mm.Hg lasting 19 minutes and 21 minutes respectively at doses of 0.5 and 1 $\mu$g./kg. animal body weight respectively, 16-cyclohexyl-$\omega$-trinor $PGE_1$ methyl ester produces falls in blood pressure of 22 mm.Hg, and 38 mm.Hg lasting 13 minutes and 20 minutes respectively at doses of 0.2 and 0.5 $\mu$g./kg. animal body weight respectively, 16-cyclohexyl-$\omega$-trinor-$PGE_1$ isobutyl ester produces falls in blood pressure of 22 mm.Hg and 42 mm.Hg lasting 10 minutes and 24 minutes respectively at doses of 0.2 and 0.5 $\mu$g./kg. animal body weight respectively, 16-cyclohexyl-$\omega$-trinor-$PGE_1$ decyl ester produces a fall in blood pressure of 40 mm.Hg lasting 100 minutes at a dose of 50 $\mu$g./kg. animal body weight, 16-cyclopentyl-$\omega$-trinor-$PGE_2$ produces falls in blood pressure of 10 mm.Hg and 68 mm.Hg lasting 8 minutes and 13 minutes respectively at doses of 2 and 5 $\mu$g./kg. animal body weight respectively, 16-cyclopentyl-$\omega$-trinor-15-epi-$PGE_2$ produces falls in blood pressure of 12 mm.Hg, 18 mm.Hg and 60 mm.Hg lasting 9 minutes, 8 minutes and 19 minutes respectively at doses of 1, 2 and 5 $\mu$g./kg. animal body weight respectively, and 16-cyclopentyl-$\omega$-trinor-$PGA_2$ produces falls in blood pressure of 16 mm.Hg and 28 mm.Hg lasting 11 minutes and 18 minutes respectively at doses of 1 and 2 $\mu$g./kg animal body weight respectively; (ii) 50 percent inhibition of adenosine diphosphate - induced blood platelet aggregation in platelet-rich plasma of rats is produced by 16-cyclohexyl-$\omega$-trinor-$PGE_1$ decyl ester at a dose of $1.7 \times 10^{-1}\mu$g./ml., by 16-cyclohexyl-$\omega$-trinor-$PGE_1$ at a dose of $3.0 \times 10^{-2}\mu$g./ml., by 16-cyclohexyl-$\omega$-trinor-$PGE_1$ methyl ester at a dose of $7.2 \times 10^{-2}\mu$g./ml. and by 16-cyclohexyl-$\omega$-trinor-$PGE_1$ isobutyl ester at a dose of $7.8 \times 10^{-2}\mu$g./ml. in comparison with controls, the corresponding dose for $PGE_1$ being $5.2 \times 10^{-2}\mu$g./ml.; (iii) 50 percent inhibition of adenosine diphosphate - induced blood platelet aggregation in platelet-rich human plasma is produced by 16-cyclohexyl-$\omega$-trinor-$PGE_1$ at a dose of $5.4 \times 10^{-2}\mu$g./ml. in comparison with controls, the corresponding dose for $PGE_1$ being $1.1 \times 10^{-2}\mu$g./ml.; (iv) is stress ulceration of rats produced according to the method of Takagi and Okabe [Jap. J. Pharmac. 18, 9–18 (1968)], 16-cyclohexyl-$\omega$-trinor-$PGE_2$ produces 62.0% inhibition of stress ulceration at a dose of 50$\mu$g./kg. animal body weight by oral administration and 16-cyclohexyl-$\omega$-trinor-$PGE_1$ produces 26.2%, 60.3% and 58.4% inhibition of stress ulceration at doses of 50, 100 and 200 $\mu$g./kg. animal body weight respectively, by oral administration; (v) against the increase in resistance in the respiratory tract of the guinea pig induced by the administration of histamine, as determined by the method of Konzett and Rossler [Arch. exp. Path. Pharmak. 105, 71–74 (1940)], 16-cyclohexyl-$\omega$-trinor-$PGE_1$ decyl ester produces an inhibition of 47.4% at a dose of 20 $\mu$g./kg. animal body weight by intravenous administration, 16-cyclohexyl-$\omega$-trinor-$PGE_1$ methyl ester produces inhibitions of 71.4%, 73.3% and 70.0% at doses of 0.05, 0.1 and 0.5$\mu$g./kg. animal body weight respectively by intravenous administration, 16-cyclohexyl-$\omega$-trinor-$PGE_1$ isobutyl ester produces inhibitions of 80.5% and 75.5% at doses of 0.05 and 0.1$\mu$g./kg. animal body weight respectively by intravenous administration, 16-cyclopentyl-$\omega$-trinor-$PGE_2$ produces inhibitions of 58.5% and 84.1% at doses of 0.05 and 0.1$\mu$g./kg. animal body weight respectively by intravenous administration and 16-cyclopentyl-$\omega$-trinor-15-epi-$PGE_2$ produces inhibitions of 68.35 and 82.4% at doses of 0.5 and 1.0$\mu$g./kg animal body weight respectively by intravenous administration; (vi) when administered subcutaneously twice daily at a dose of 5 $\mu$g./kg. animal body weight to hysterectomised Wistar-strain female rats, 16-cyclohexyl-$\omega$-trinor-$PGF_{2\alpha}$ exhibits luteolytic activity, prducing a 60% efficacy in restoring oestrus in comparison with controls within a period of 5.2 ± 0.4 days post-hysterectomy, the corresponding period for the controls being 10.7 ± 0.7 days post-hysterectomy, while 16-cyclopentyl-$\omega$-trinor-$PGF_{2\alpha}$ when similarly administered at a dose of 25$\mu$g./kg. animal body weight exhibits a 42.9% efficacy in restoring oestrus in comparison with the controls within a period of 6.3 ± 0.5 days post-hysterectomy; (vii) 16-cyclohexyl-$\omega$-trinor-$PGE_{2\alpha}$ exhibits luteolytic activity when administered twice daily to HCG-treated female rabbits (30 IU/kg. animal body weight administered intravenously per animal) from the 5th to 15th days after HCG administration, as shown by determination of the mean ovarian weight and mean corpus luteum volume on the 16th day after HCG administration, the mean ovarian weights being 728.9 ± 165.5 mg. and 945.6 ± 220.5 mg. and the mean corpus luteum volumes being 158.5 ± 82.9 mm$^3$ and 119.2 ± 51.8 mm$^3$ at doses of 10 and 50μg./kg. animal body weight respectively, the mean ovarian weight of the controls being 819.3 ± 170.8 mg. and the mean corpus luteum volume of the controls being 345.7 ± 113.7 mm$^3$; (viii) 16-cyclohexyl-ω-trinor-PGF$_{2\alpha}$, by intravenous administration to the pregnant rat, has an effective dose of 500.0 ± 0μg./kg. animal body weight in inducing uterine contraction, as determined by the effect on intrauterine pressure, and (ix) 16-cyclohexy-ω-trinor-PGF$_{2\alpha}$ exhibits a stimulatory effect in vitro on the isolated uterus of the ovariectomised rat, producing 50% contraction at a dose of 3.2 × 10$^{-8}$g./ml.

The prostaglandin compounds of the present invention and their cyclodextrin clathrates and non-toxic salts have relatively low potencies in inducing diarrhoea in comparison with their potencies in respect of the valuable properties hereinbefore described; for example the doses of 16-cyclohexyl-ω-trinor-PGE$_1$, 16-cyclohexyl-ω-trinor-PGE$_2$, 16-cyclopentyl-ω-trinor-PGE$_2$ and 16-cyclopentyl-ω-trinor-15-epi-PGE$_2$ required to produce diarrhoea in 50% of mice so treated are 2300, 560, 2200 and 10500 μg./kg. animal body weight respectively.

Classes of compounds of general formula VII which may specifically be mentioned are those wherein X represents —CH$_2$CH$_2$— or cis —CH=CH—, Y represents trans —CH=CH—, A represents a straight- or branched-chain alkyl radical containing from 1 to 3 carbon atoms (preferably —CH(CH$_3$)— or —CH$_2$CH$_2$—) and n represents 4 or, when A represents a branched-chain alkyl radical containing 2 or 3 carbon stoms (preferably —CH(CH$_3$)—), n represents 5, and ∿ indicates attachment of the hydroxy radical to the carbon atom in alpha or beta configuration, and those wherein X and Y each represent —CH$_2$CH$_2$—, A represents a straight- or branched-chain alkyl radical containing from 1 to 3 carbon atoms (preferably —CH(CH$_3$)— or —CH$_2$CH$_2$—), n represents 4 or 5 and∿ indicates attachment of the hydroxy radical to the carbon atom in alpha or beta configuration, and alkyl esters thereof having from 1 to 12 carbon atoms in a straight- or branched-chain, and cyclodextrin clathrates of such acids and esters and non-toxic salts of such acids of general formula VII.

The following Reference Examples and Examples illustrate the process of the present invention and products thereof.

REFERENCE EXAMPLE 1

Dimethyl 3-cyclohexyl-2-oxo-butylphosphonate 74.5 g. of dimethyl methylphosphonate were dissolved in 514 ml. of tetrahydrofuran and the solution cooled to −60°C. To this solution a solution of butyllithium [prepared from 40.5 g. of butyl bromide and 9.2 g. of lithium] in 240 ml. of diethyl ether was added dropwise. A solution of 39.5 g. of ethyl 2-cyclohexyl-propionate in 130 ml. of tetrahydrofuran was added drop-wise and the mixture stirred at the same temperature for two hours and afterwards at 0°C. overnight. The reaction mixture was then neutralised to pH 7 with acetic acid, concentrated under reduced pressure and, after the addition of water to the residue, extracted with diethyl ether. After drying the ethereal extract, the solvent was distilled off and the residue subjected to distillation under reduced pressure to obtain 40 g. (yield 30.2%) of the title compound as a colourless oil, b.p. 140°C./0.2–0.3 mm.Hg. Nuclear magnetic resonance (hereinafter abbreviated to NMR) spectrum (tetrachloromethane): δ = 3.82 (6 H, doublet, 3.18 (2H, doublet), 2.80 – 2.30 (1H, multiplet), 2.1 – 0.65 (14H, multiplet).

REFERENCE EXAMPLE 2

Dimethyl 4-cyclohexyl-2-oxo-butylphosphonate 135 g. of dimethyl methylphosphonate were dissolved in 800 ml. of tetrahydrofuran, and to the solution cooled to −65°C., a solution of butyllithium [prepared from 163 g. of butyl bromide and 16 g. of lithium] in 610 ml. of diethyl ether was added drop-wise. To the reaction mixture was added drop-wise a solution of 62.5 g. of ethyl 3-cyclohexylpropionate in 300 ml. of tetrahydrofuran and the resulting mixture was stirred at the same temperature for two hours and afterwards at 0°C., overnight. The reaction mixture was then neutralised with acetic acid, concentrated under reduced pressure and after the addition of water extracted with diethyl ether. The ethereal extract was dried and the solvent distilled off. The residue was subjected to distillation under reduced pressure to obtain 51 g. (yield 52.3%) of the title product as a colourless oil, b.p. 143°–148°C./0.2 – 0.4 mm.Hg. NMR spectrum (tetrachloromethane): δ = 3.82 (6H, doublet), 3.16 (2H, doublet), 2.4 (2H, triplet), 1.97 – 1.08 (13H, multiplet).

REFERENCE EXAMPLE 3

Dimethyl 4-cyclopentyl-2-oxo-butylphosphonate 125 g. of dimethyl methylphosphonate were dissolved in 720 ml. of tetrahydrofuran and the solution cooled to −65°C. To this solution a solution of butyllithium [prepared from 150 g. of butyl bromide and 14.5 g. of lithium] in 550 ml. of diethyl ether was added dropwise. To the mixture a solution of 52.5 g. of ethyl 3-cyclopentylpropionate in 280 ml. of tetrahydrofuran was added drop-wise and the reaction mixture was stirred at the same temperature for 2 hours and afterwards at 0°C. overnight. The reaction mixture was then neutralised with acetic acid, concentrated under reduced pressure and the resulting residue after the addition of water was extracted with diethyl ether. The ethereal extract was dried over sodium sulphate, the solvent distilled off and the residue distilled under reduced pressure to obtain 47 g. (yield 61.2%) of the title compound as a colourless oil, b.p. 142°– 144°C./0.4 – 0.5 mm.Hg. NMR spectrum (tetrachloromethane): δ = 3.84 (6H, doublet), 3.19 (2H, doublet), 2.42 (2H, triplet), 2.0 – 1.09 (11H, multiplet).

REFERENCE EXAMPLE 4

2-Oxa-3-oxo-6-syn-(3-oxo-4-cyclohexylpent-trans-1-enyl)-7-anti-acetoxy-cis-bicyclo[3,3,0]octane 5.7 g. of sodium hydride (content 63.9%) were suspended in 850 ml. of tetrahydrofuran, and a solution of 40 g. of dimethyl 3-cyclohexyl-2-oxo-butylphosphonate [prepared as described in Reference Example 1] in 170 ml. of tetrahydrofuran was added. Hydrogen was vigorously generated and the solution became a clear yellow. Into the solution a solution of 32.4 g. of 2-oxa-3-oxo-6-syn-formyl-7-anti-acetoxy-cis-bicyclo[3,3,-0]octane in 80 ml. of tetrahydrofuran was introduced and the reaction mixture stirred at room temperature for an hour. It was then neutralised with acetic acid and the resulting precipitate removed by filtration. The filtrate was concentrated under reduced pressure, and the residue purified by means of silica gel column chromatography using as eluent a mixture of ethyl acetate and benzene (1:6) to obtain the title compound as a pale yellow oil in an amount of 32 g. (yield 48%). Thin layer chromatography (hereinafter abbreviated to TLC) (benzene:ethyl acetate = 4:1): Rf = 0.55; NMR spectrum (CDCl$_3$): δ = 6.78 (1H, quartet), 6.25 (1H, doublet), 5.54 – 4.92 (2H, multiplet), 1.99 (3H, singlet); Infra-red (hereinafter abbreviated to IR) absorption spectrum (liquid film): 2900, 1760, 1735 and 1675 cm$^{-1}$.

REFERENCE EXAMPLE 5

2-Oxa-3-oxo-6-syn-(3-oxo-5-cyclohexylpent-trans-1-enyl)-7-anti-acetoxy-cis-bicyclo-[3,3,0]octane 7.3 g. of sodium hydride (content 63.9%) were suspended in 1 liter of tetrahydrofuran and a solution of 51 g. of dimethyl 4-cyclohexyl-2-oxo-butylphosphonate [prepared as described in Reference Example 2] in 210 ml. of tetrahydrofuran was added and the mixture stirred for 20 minutes. A solution of 41.3 g. of 2-oxa-3-oxo-6-syn-formyl-7-anti-acetoxy-cis-bicyclo[3,3,0]octane in 100 ml. of tetrahydrofuran was then added and the reaction mixture stirred at room temperature for 1.5 hours. Afterwards the reaction mixture was treated in accordance with the procedure of Reference Example 4 to obtain the title product as a pale yellow oil in an amount of 38.1 g. (yield 55.8%). TLC (benzene:methanol:diethyl ether = 5:1:1): Rf = 0.72; NMR spectrum (CDCl$_3$): δ = 6.76 (1H, quartet), 6.23 (1H, doublet), 5.4 – 4.91 (2H, multiplet), 2.02 (3H, singlet).

REFERENCE EXAMPLE 6

2-Oxa-3-oxo-6-syn-(3-oxo-5-cyclopentyl-pent-trans-1-enyl)-7-anti-acetoxy-cis-bicyclo[3,3,0]octane Following the same procedures as described in Reference Examples 5 and 6 but using 40 g. of 2-oxa-3-oxo-6-syn-formyl-7-anti-acetoxy-cis-bicyclo[3,3,0]octane and 47 g. of dimethyl 4-cyclopentyl-2-oxo-butylphosphonate [prepared as described in Reference Example 3], the title compound was obtained as a pale yellow oil in an amount of 34 g. (yield 53.5%). TLC (benzene:methanol:diethyl ether = 5:1:1): Rf = 0.68; IR absorption spectrum (liquid film): 2950 – 2850, 1770, 1740 and 1675 cm$^{-1}$; NMR spectrum (CDCl$_3$): δ = 6.78 (1H, quartet), 6.25 (1H, doublet), 5.43 – 4.92 (2H, multiplet), 2.02 (3H, singlet).

REFERENCE EXAMPLE 7

2-Oxa-3-oxo-6-syn-(3-hydroxy-4-cyclohexylpent-trans-1-enyl)-7-anti-acetoxy-cis-bicyclo[3,3,0]octane 32 g. of 2-oxa-3-oxo-6-syn-(3-oxo-4-cyclohexyl-pent-trans-1-enyl)-7-anti-acetoxy-cis-bicyclo[3,3,-0]octane, prepared as described in Reference Example 4, were dissolved in 310 ml. of methanol, and 10.5 g. of sodium borohydride were added whilst keeping the internal temperature at −40°C. After 10 minutes, the mixture was neutralised with acetic acid and then concentrated under reduced pressure. The resulting residue was dissolved in ethyl acetate, and the solution was washed successively with a saturated aqueous solution of sodium bicarbonate and brine, and then dried. The solvent was distilled off and the resulting residue subjected to column chromatography to separate the fraction having an α-hydroxy group in the product from that having a β-hydroxy group. As eluent a mixture of diethyl ether, ethyl acetate and cyclohexane [2:1:1] was used to obtain 9 g. of α-hydroxy compound and 12 g. of β-hydroxy compound, and a mixture analysis: both in the amount of 6 g. TLC (developed twice with diethyl ether): α-hydroxy compound; Rf = 0.75, β-hydroxy compound; Rf = 0.67; α-hydroxy compound is a white crystalline substance melting at 128° to 130°C.; NMR spectrum (CDCl$_3$): δ = 5.60 – 5.30 (2H, multiplet), 5.14 – 4.63 (2H, multiplet), 4.2 – 3.85 (1H, multiplet), 2.0 (3H, singlet).

Elemental analysis: C$_{20}$H$_{30}$O$_5$
Calculated value: C, 68.54%; H, 8.63%
Found: C, 68.48%; H, 8.61%

REFERENCE EXAMPLE 8

2-Oxa-3-oxo-6-syn-(3-hydroxy-5-cyclohexylpent-trans-1-enyl)-7-anti-acetoxy-cis-bicyclo[3,3,0]octane The same procedure as in Reference Example 7 was followed using 38 g. of 2-oxa-3-oxo-6-syn-(3-oxo-5-cyclohexylpent-trans-1-enyl)-7-anti-acetoxy-cis-bicyclo[3,3,0]octane, prepared as described in Reference Example 5, and 12 g. of sodium borohydride 10.3 g. of the title compound were obtained. TLC (chloroform:methanol = 20:1): Rf = 0.64, (developed twice with diethyl ether): Rf = 0.73; NMR spectrum (CDCl$_3$): δ = 5.55 – 5.28 (2H, multiplet), 5.10 – 4.65 (3H, multiplet), 4.15 – 3.75 (1H, multiplet), 2.0 (3H, singlet).

REFERENCE EXAMPLE 9

2-Oxa-3-oxo-6-syn-(3-hydroxy-5-cyclopentyl-pent-trans-1-enyl)-7-anti-acetoxy-cis-bicyclo[3,3,0]octane The same procedure as in Reference Example 7 was followed using 34 g. of 2-oxa-3-oxo-6-syn-(3-oxo-5-cyclo-pentyl-pent-trans-1-enyl)-7-anti-acetoxy-cis-bicyclo[3,3,0]octane, prepared as described in Reference Example 6, as starting material to obtain 9.8 g. of the title compound. TLC (developed twice with diethyl ether): Rf = 0.71; NMR spectrum (CDCl$_3$): δ = 5.56 – 5.31 (2H, multiplet), 5.12 – 4.60 (2H, multiplet), 4.33 – 3.72 (2H, multiplet), 2.02 (3H, singlet); IR absorption spectrum (liquid film): 3400, 2950– 2850, 1760, 1735, 1420, 1360, 1240 and 1160 cm$^{-1}$.

REFERENCE EXAMPLE 10

2-Oxa-3-hydroxy-6-syn-[3-(2-tetrahydropyranyloxy)-4-cyclohexylpent-trans-1-enyl]-7-anti-(2-tetrahydropyranyloxy)-cis-bicyclo[3,3,0]octane 9 g. of 2-oxa-3-oxo-6-syn-(3-hydroxy-4-cyclohexyl-pent-trans-1-enyl)-7-anti-acetoxy-cis-bicyclo[3,3,-0]octane, prepared as described in Reference Example 7, were stirred with a solution of 4 g. of potassium carbonate in 95 ml. of methanol at 25°C. for 30 minutes to obtain 2-oxa-3-oxo-6-syn-(3-hydroxy-4-cyclohexylpent-trans-1-enyl)-7-anti-hydroxy-cis-bicyclo[3,3,0]octane as a white crystalline solid in an amount of 6.5 g. (Yield 82.2%). This diol was dissolved in 72 ml. of methylene chloride to which 66 mg. of p-toluenesulphonic acid and 5.6 g. of dihydropyran had been added, and the reaction mixture was stirred at room temperature for 15 minutes to obtain 10.5 g. of the bis-tetrahydropyranyl ether in the form of a yellow oil.

The bis-tetrahydropyranyl ether was dissolved in 100 ml. of toluene and, after cooling the solution to −60°C., 2 equimolar amounts of diisobutylaluminium hydride were added with stirring. After subjecting the said ether to reduction for 30 minutes, the title compound was obtained in a yield of 10 g. and as a pale yellow oil. TLC (methylene chloride:methanol = 20:1): Rf = 0.38; NMR spectrum (CDCl$_3$): δ = 5.7 – 5.32 (3H, multiplet), 4.85–4.30 (3H, multiplet), 4.2–3.2 (7H, multiplet).

REFERENCE EXAMPLE 11

2-Oxa-3-hydroxy-6-syn-[3-(2-tetrahydropyranyloxy)-5-cyclohexylpent-trans-1-enyl]-7-anti-(2-tetrahydropyranyloxy)-cis-bicyclo[3,3,0]octane The same procedure as in Reference Example 10 was followed using 12 g. of 2-oxa-3-oxo-6-syn-(3-hydroxy-5-cyclohexylpent-trans-1-enyl)-7-anti-acetoxy-cis-bicyclo[3,3,0]octane, prepared as described in Reference Example 8, as starting material. The title compound was obtained in a yield of 12.4 g. as a yellow oil. TLC (methylene chloride:methanol = 20:1): Rf = 0.41; NMR spectrum (CDCl$_3$): δ = 5.72 – 5.25 (3H, multiplet), 4.84 – 4.58 (2H, multiplet), 4.58 – 4.34 (1H, multiplet), 4.26 – 3.3 (7H, multiplet).

Elemental analysis: C$_{28}$H$_{46}$O$_6$
Calculated value: C, 70.26%; H, 9.69%
Found: C, 70.14%; H, 9.61%

REFERENCE EXAMPLE 12

2-Oxa-3-hydroxy-6-syn-[3-(2-tetrahydropyranyloxy)-5-cyclopentyl-pent-trans-1-enyl]-7-anti-(2-tetrahydropyranyloxy)-cis-bicyclo[3,3,0]octane The same procedure as in Reference Example 10 was followed using 9.5 g. of 2-oxa-3-oxo-6-syn-(3-hydroxy-5-cyclopentyl-pent-trans-1-enyl)-7-anti-acetoxy-cis-bicyclo[3,3,0]octane, prepared as described in Reference Example 9, as starting material. The title compound was obtained in a yield of 12.6 g. as a pale yellow oil. TLC (methylene chloride:methanol = 20:1): Rf = 0.39; NMR spectrum (CDCl$_3$): δ = 5.7 – 5.33 (3H, multiplet), 4.80 – 4.30 (3H, multiplet), 4.22 – 3.3 (7H, multiplet).

Elemental analysis: C$_{27}$H$_{44}$O$_6$
Calculated value: C, 69.79%; H, 9.55%
Found: C, 69.91%, H, 9.57%.

EXAMPLE 1

9α-Hydroxy-11α,15α-di-(2-tetrahydropyranyloxy)-16-cyclohexyl-ω-trinor-prosta-cis-5, trans-13-dienoic acid 3.74 g. of sodium hydride (content 63.9%) was suspended in 41.4 ml. of dimethylsulphoxide and the suspension heated to 72°– 75°C., with stirring to obtain sodiomethylsulphinylcarbanide; the reaction mixture was cooled to room temperature.

To a solution of 24.3 g. of 4-carboxy-n-butyltriphenylphosphonium bromide in 54.6 ml. of dimethylsulphoxide the obtained sodiomethylsulphinyl/carbanide solution was added drop-wise whilst keeping the temperature at 20° to 30°C. After stirring for 5 minutes, a solution of 10 g. of 2-oxa-3-hydroxy-6-syn-[3-(2-tetrahydropyranyloxy)-4-cyclohexylpent-trans-1-enyl]-7-anti-(2-tetrahydropyranyloxy)-cis-bicyclo[3,3,0]octane, prepared as described in Reference Example 10, in 20 ml. of dimethylsulphoxide was added all at once and the reaction mixture was vigorously stirred for 2 hours.

The reaction mixture was then poured into ice-water, and extracted with a mixture of diethyl ether and ethyl acetate [1:1] to remove the neutral substances. The aqueous layer was neutralised with oxalic acid and the acidic layer extracted with a mixture of diethyl ether and pentane [1:1]. The organic layer after separation was washed, dried and the solvent removed. The resulting residue was purified by means of silica gel column chromatography using as eluent a benzene-ethanol mixture [100:5]. The title compound was obtained as a pale yellow oil in an amount of 5 g. (yield 44.6%). TLC (methylene chloride:methanol = 20:1): Rf = 0.32; IR absorption spectrum (liquid film): 3400, 2950 – 2860, 2400, 1705 and 1440 cm$^{-1}$; NMR spectrum (CDCl$_3$): δ = 6.2 – 5.1 (6H, multiplet), 4.80 – 4.40 (2H, multiplet), 4.20 – 3.10 (7H, multiplet).

EXAMPLE 2

9α-Hydroxy-11α,15α-di-(2-tetrahydropyranyloxy)-17-cyclohexyl-ω-trinor-prosta-cis-5, trans-13-dienoic acid The same reaction and working-up procedures as described in Example 1 were carried out using 12 g. of 2-oxa-3-hydroxy-6-syn-[3-(2-tetrahydropyranyloxy)-5-cyclohexylpent-trans-1-enyl]-7-anti-(2-tetrahydropyranyloxy)-cis-bicyclo[3,3,0]octane, prepared as described in Reference Example 11, as a starting material. 8.7 g. (yield 61.6%) of the title compound were obtained. TLC (methylene chloride:methanol = 20:1): Rf = 0.31; NMR spectrum (CDCl$_3$): δ = 6.7 – 5.9 (2H, broad singlet), 5.67 – 5.15 (4H, multiplet), 4.9 – 4.55 (2H, multiplet), 4.25 – 3.20 (7H, multiplet).

EXAMPLE 3

9α-Hydroxy-11α,15α-di-(2-tetrahydropyranyloxy)-17-cyclopentyl-ω-trinor-prosta-cis-5, trans-13-dienoic acid The same reaction and working-up procedures as described in Example 1 were carried out using 9.2 g. of 2-oxa-3-hydroxy-6-syn-[3-(2-tetrahydropyranyloxy)-5-cyclopentyl-pent-trans-1-enyl]-7-anti-(2-tetrahydropyranyloxy)-cis-bicyclo[3,3,0]octane, prepared as described in Reference Example 12, as a starting material. 6.5 g. (yield 55.7%) of the title compound were obtained. TLC (methylene chloride:methanol = 20:1): Rf = 0.34; NMR spectrum (CDCl$_3$): δ = 6.4 – 5.7 (2H, broad singlet), 5.6 – 5.12 (4H, multiplet), 4.8 – 4.45 (2H, multiplet), 4.21 – 3.18 (7H, multiplet).

EXAMPLE 4

9α-Hydroxy-11α,15α-di-(2-tetrahydropyranyloxy)-16-cyclohexyl-ω-trinor-prost-trans-13-enoic acid 0.3 g. of 5% palladium on carbon was suspended in 3ml. of methanol and, after the air inside the vessel had been replaced with hydrogen, a solution of 1 g. of 9α-hydroxy-11α,15α-di-(2-tetrahydropyranyloxy)-16-cyclohexyl-ω-trinor-prosta-cis-5, trans-13-dienoic acid [prepared as described in Example 1] in 5 ml. of methanol was added to the suspension. Catalytic reduction of the starting material was carried out at room temperature and atmospheric pressure. When the required theoretical amount of hydrogen had been absorbed, the reaction was terminated and the catalyst removed by filtration. The filtrate was concentrated under reduced pressure. A part of the resulting concentrate was hydrolysed with 0.1N hydrochloric acid at 75°C. for 5 minutes. The hydrolysis product was extracted with an organic solvent. The extract was developed on a silica-gel plate which had been pre-treated with silver nitrate and, as a developing solvent, the upper layer of a mixture of ethyl acetate, isooctane, acetic acid and water (110:30:20:100) was used. At the time TLC Rf value was 0.38.

When the starting material was hydrolysed in a similar way to that described above, the Rf value was 0.24. Yield of the title compound was 740 mg. NMR spectrum (CDCl$_3$): δ = 6.33 – 5.75 (2H, broad singlet), 5.50 – 5.07 (2H, multiplet), 4.75 – 4.40 (2H, multiplet), 4.20 – 3.08 (7H, multiplet).

Following the same procedure as in Example 4, the following compounds were obtained:

A.

9α-Hydroxy-11α,15α-di-(2-tetrahydropyranyloxy)-17-cyclohexyl-ω-trinor-prost-trans-13-enoic acid 1.03 g. of the title compound was obtained using as starting material 1.2 g. of the product of Example 2.

When the hydrolysis product of the resulting product and of the starting material (using as the hydrolysing agent dilute hydrochloric acid) were subjected to thin layer chromatography using a silica-gel plate pre-treated with silver nitrate, the Rf values are 0.39 and 0.27 respectively.

B.

9α-Hydroxy-11α,15α-di-(2-tetrahydropyranyloxy)-17-cyclopentyl-ω-trinor-prost-trans-13-enoic acid Using as starting material 1.41 g. of the product of Example 3, 1.2 g. of the title compound were obtained.

When the hydrolysis product of the resulting product and the starting material (using as hydrolysing agent dilute hydrochloric acid) were subjected to thin layer chromatography on a silica-gel plate pre-treated with silver nitrate, their Rf values were 0.41 and 0.29 respectively.

EXAMPLE 5

9α-Hydroxy-11α,15α-di-(2-tetrahydropyranyloxy)-16-cyclohexyl-ω-trinor-prostanoic acid 940 mg. of 9α-hydroxy-11α,15α-di-(2-tetrahydropyranyloxy)-16-cyclohexyl-ω-trinor-prosta-cis-5, trans-13-dienoic acid (prepared as described in Example 1) in 10 ml. of ethanol were subjected to catalytic hydrogenation in the presence of 85 mg. of platinum oxide until absorption of hydrogen ceased.

After the reaction the catalyst was filtered off and the resulting filtrate evaporated to dryness under reduced pressure. A part of the residue was hydrolysed with 0.1N hydrochloric acid at 75°C. for 5 minutes, and the hydrolysis product extracted with an organic solvent. The extract was subjected to thin layer chromatography using a silica-gel plate pre-treated with silver nitrate. As the developing solvent, the upper layer of a mixture of ethyl acetate, isooctane, acetic acid and water (110:30:20:100) was used. The Rf values of the hydrolysis product of the resulting product and the starting material were 0.42 and 0.24 respectively. According to the NMR spectrum the signal of hydrogen of a double bond near to δ = 5.5 disappeared. Yield of the title compound was 835 mg.

By the same procedure as described in Example 5, the following compounds were obtained from the corresponding prosta-cis-5, trans-13-dienoic acids, i.e. the products of Examples 2 and 3.

A.

9α-Hydroxy-11α,15α-di-(2-tetrahydropyranyloxy)-17-cyclohexyl-ω-trinor-prostanoic acid

B.

9α-Hydroxy-11α,15α-di-(2-tetrahydropyranyloxy)-17-cyclopentyl-ω-trinor-prostanoic acid The products (A) and (B) were identified by thin layer chromatography and their NMR spectra.

EXAMPLE 6

16-Cyclohexyl-ω-trinor-PGF$_2$α

250 mg. of 9α-hydroxy-11α,15α-di-(2-tetrahydropyranyloxy)-16-cyclohexyl-ω-trinor-prosta-cis-5, trans-13-dienoic acid (prepared as described in Example 1) were dissolved in a mixture of 0.23 ml. of 12N hydrochloric acid, 1.7 ml. of water and 1.9 ml. of tetrahydrofuran, and stirred at 25°C. for 3 hours. 156 mg. of sodium bicarbonate and a small amount of water were added. The reaction mixture was then extracted with ethyl acetate. The organic layer was washed with saturated brine, dried, evaporated to dryness under reduced pressure and the residue purified by silica gel column chromatography. As eluent a mixture of ethyl acetate and cyclohexane [3:2] was used. 62 mg. of the title compound in pure form (a colourless oil) was obtained. TLC (chloroform:tetrahydrofuran:acetic acid = 10:2:1); Rf = 0.20; NMR spectrum (CDCl$_3$): δ = 5.65 – 5.26 (4H, multiplet), 5.05 – 4.56 (4H, broad singlet), 4.31 – 3.80 (3H, multiplet), 1.0 – 0.7 (3H, multiplet).

Elemental analysis: $C_{23}H_{38}O_5$

Calculated value: C, 70.01%: H, 9.71%

Found: C, 79.9%; H, 9.68%

EXAMPLE 7

17-Cyclohexyl-ω-trinor-PGF$_2$α

302 mg. of 9α-hydroxy-11α,15α-di-(2-tetrahydropyranyloxy)-17-cyclohexyl-ω-trinor-prosta-cis-5, trans-13-dienoic acid (prepared as described in Example 2) were dissolved in 8 ml. of a mixture of acetic acid, water and tetrahydrofuran (65:35:10) and stirred at 46°C., for 3 hours. The solvent was distilled off under reduced pressure, the resulting residue dissolved in ethyl acetate, and the solution washed with water. The solution was evaporated to dryness and purified by chromatography as described in Example 6 to obtain 86 mg. of the title compound. TLC (chloroform:tetrahydrofuran:acetic acid = 10:2:1): Rf = 0.21; NMR spectrum (CDCl$_3$): δ = 5.70 – 5.25 (4H, multiplet, 4.98 – 4.55 (4H, broad singlet), 4.28 – 3.81 (3H, multiplet), 1.95 – 0.95 (multiplet).

Elemental analysis: $C_{23}H_{38}O_5$

Calculated value: C, 70.01%; H, 9.71%

Found: C, 69.89%; H, 9.67%.

The following compounds (A) to (G) were prepared in a similar manner to the procedures described in Examples 6 and 7. (The developing solvent for TLC was the same as in the previous instances unless otherwise particularly specified).

A. 16-Cyclohexyl-ω-trinor-PGF$_{1\alpha}$

TLC : Rf = 0.20; NMR spectrum (CDCl$_3$): δ = 5.65 − 5.40 (2H, multiplet), 5.1 − 4.60 (4H, broad singlet), 4.30 − 3.75 (3H, multiplet), 1.02 − 0.7 (3H, mutliplet).
Elemental analysis: C$_{23}$H$_{40}$O$_5$
Calculated value C, 69.66%; H, 10.17%
Found: C, 69.64%; H 10.20%

B. 16-Cyclohexyl-ω-trinor-13,14-dihydro-PGF$_{1\alpha}$

TLC (ethyl acetate:formic acid = 400:5): Rf = 0.32; NMR spectrum CDCl$_3$): δ = 4.98 − 4.56 (4H, broad singlet), 4.29 − 3.85 (2H, multiplet), 3.63 − 3.35 (1H, multiplet), 2.33 (2H, triplet), 1.0 − 0.7 (3H, multiplet).
Elemental analysis C$_{23}$H$_{42}$O$_5$
Calculated value: C, 69.31%; H, 10.62%
Found: C, 69.22%; H, 10.56%

C. 17-Cyclohexyl-ω-trinor-PGF$_{1\alpha}$

TLC: Rf = 0.20; NMR spectrum (CDCl$_3$): δ = 5.62 − 5.39 (2H, multiplet), 5.05 − 4.53 (4H, broad singlet), 4.27 − 3.75 (3H, multiplet), 1.93 − 1.03 (multiplet).
Elemental analysis: C$_{23}$H$_{40}$O$_5$
Calculated value C, 69.66%; H, 10.17%
Found: C, 69.57%; H, 10.12%

D. 17-Cyclohexyl-ω-trinor-13,14-dihydro-PGF$_{1\alpha}$

TLC (ethyl acetate:formic acid = 400:5): Rf = 0.31; NMR spectrum (CDCl$_3$): δ= 5.0 − 4.56 (4H, broad singlet), 4.25 − 3.87 (2H, multiplet), 3.64 − 3.36 (1H, multiplet), 2.31 (2H, triplet), 1.93 − 1.03 (multiplet).
Elemental analysis C$_{23}$H$_{42}$O$_5$
Calculated value: C, 69.31% H, 10.62%
Found: C, 69.18%, H, 10.54%

E. 17-Cyclopentyl-ω-trinor-PGF$_{2\alpha}$

TLC: Rf = 0.22; NMR spectrum (CDCl$_3$): δ= 5.67 − 5.23 (4H, multiplet), 5.05 − 4.60 (4H, broad singlet), 4.27 − 3.83 (3H, multiplet).
Elemental analysis: C$_{22}$H$_{36}$O$_5$
Calculated value: C, 69.44%; H, 9.54%
Found: C, 69.49%; H, 9.52%

F. 17-Cyclopentyl-ω-trinor-PGF$_{1\alpha}$

TLC:Rf = 0.21; NMR spectrum (CDCl$_3$): δ = 5.63 − 5.36 (2H, multiplet), 4.98 − 4.46 (4H, broad singlet), 4.26 − 3.76 (3H, multiplet).
Elemental analysis: C$_{22}$H$_{38}$O$_5$
Calculated value: C, 69.07%; H, 10.01%
Found: C, 68.93%; H, 9.94%

G. 17-Cyclopentyl-ω-trinor-13,14-dihydro-PGF$_{1\alpha}$

TLC (ethyl acetate:formic acid = 400:5): Rf = 0.28; NMR spectrum (CDCl$_3$): δ = 4.85 − 4.47 (4H, broad singlet), 4.26 − 4.07 (1H, multiplet), 4.07 − 3.88 (1H, multiplet), 3.63 − 3.38 (1H, multiplet), 2.31 (2H, multiplet).
Elemental analysis: C$_{22}$H$_{40}$O$_5$
Calculated value: C, 68.71%; H, 10.49%
Found: C, 68.82%; H, 10.51%.

For the preparation of starting materials for the aforementioned products refer to Examples 3, 4 and 5.

EXAMPLE 8

16-Cyclohexyl-ω-trinor-PGE$_2$ 500 mg. of 9α-hydroxy-11α,15α-di-(2-tetrahydropyranyloxy)-16-cyclohexyl-ω-trinor-prosta-cis-5, trans-13-dienoic acid (prepared as described in Example 1) were dissolved in 18 ml. of diethyl ether. Then 15 ml. of a chromic acid solution (prepared by dissolving 650 mg. of chromium trioxide, 3.1 g. of manganese sulphate and 0.72 ml. of sulphuric acid in water to make the total volume 15 ml.) was added, and the reaction mixture stirred vigorously for 3 hours whilst cooling on an ice-bath.

The aqueous layer of the reaction mixture was then separated and extracted with diethyl ether. The combined ethereal extracts were well washed with water and dried. After concentration under reduced pressure, the residue was dissolved in 8 ml. of a mixture of acetic acid, water and tetrahydrofuran (65:35:10) and stirred at 38° − 40°C., for 3 hours. The reaction mixture after the addition of a small amount of water was then concentrated under reduced pressure. The resulting concentrate was extracted with ethyl acetate, washed with water, dried and the solvent distilled off.

The resulting residue was purified by silica gel column chromatography using as eluent a mixture of cyclohexane and ethyl acetate [1:1]. 179 mg. of the pure title compound was obtained. TLC (chloroform:tetrahydrofuran:acetic acid = 10:2:1): Rf = 0.31; IR absorption spectrum (liquid film): 3400, 2950 − 2860, 1740, 1720 and 1450 cm$^{-1}$; NMR spectrum (CDCl$_3$); δ = 5.72 − 5.52 (2H, multiplet), 5.5 − 5.32 (2H, multiplet), 5.28 − 4.95 (3H, broad singlet), 4.26 − 3.90 (2H, multiplet), 2.93 − 2.57 (1H, multiplet), 1.0 − 0.7 (3H, multiplet).
Elemental analysis: C$_{23}$H$_{36}$O$_5$
Calculated value: C, 70.37%; H, 9.24%
Found: C, 70.36% ; H, 9.19%.

EXAMPLE 9

17-Cyclopentyl-ω-trinor-PGE$_2$ 653 mg. of 9α-hydroxy-11α,15α-di-(2-tetrahydropyranyloxy)-17-cyclopentyl-ω-trinor-prosta-cis-5, trans-13-dienoic acid (prepared as described in Example 3) were dissolved in 22 ml. of diethyl ether. Then 24 ml. of a chromic acid solution (prepared by dissolving 950 mg. of chromium trioxide, 6.9 g. of manganese sulphate and 1.9 g. of concentrated sulphuric acid in water to make the total volume 24 ml.) was added, and the reaction mixture vigorously stirred on an ice-bath for an hour and 50 minutes.

Thereafter the same procedure as in Example 8 was carried out to give 125 mg. of the title compound. TLC (chloroform:tetrahydrofuran:acetic acid = 10:2:1): Rf = 0.32; NMR spectrum (CDCl$_3$): δ = 5.74 − 5.53 (2H, multiplet), 5.5 − 5.3 (2H, multiplet), 5.15 − 4.79 (3H, broad singlet), 4.24 − 3.90 (2H, multiplet), 1.90 − 1.6 (1H, multiplet), 2.55 − 0.95 (multiplet).
Elemental analysis: C$_{22}$H$_{34}$O$_5$
Calculated value: C, 69.81%; H, 9.05%
Found: C, 69.68%; H, 8.98%.

The following compounds (A) to (G) were prepared in a similar manner to the procedures described in Examples 8 and 9. (The developing solvent for TLC was the same as mentioned above in this Example).

A. 16-Cyclohexyl-ω-trinor-PGE$_1$

TLC: Rf = 0.34; NMR spectrum (CDCl$_3$): δ = 6.05 − 5.25 (broad singlet), 5.60 − 5.50 (multiplet) (the both are combined to the 5H), 4.26 − 3.84 (2H, multiplet), 2.9 − 2.58 (1H, multiplet), 1.03 − 0.7 (3H, multiplet).
Elemental analysis: C$_{23}$H$_{38}$O$_5$ Calculated value: C, 70.01%; H, 9.71%
Found: C, 69.89%; H, 9.63%.

B. 16-Cyclohexyl-ω-trinor-13,14-dihydro-PGE₁

TLC: Rf = 0.43; NMR spectrum (CDCl₃): δ = 4.93 − 4.52 (3H, broad singlet), 4.28 − 4.01 (1H, multiplet), 3.67 − 3.42 (1H, multiplet), 2.88 − 2.57 (1H, multiplet), 1.0 − 0.73 (3H, multiplet).
Elemental analysis: $C_{23}H_{40}O_5$
Calculated value: C, 69.66%; H, 10.17%
Found: C, 69.62%; H, 10.15%.

C. 17-Cyclopentyl-ω-trinor-PGE₁

TLC: Rf = 0.32; NMR spectrum (CDCl₃): δ = 5.87 − 5.12 (5H, multiplet), 4.27 − 3.86 (2H, multiplet), 2.9 − 2.55 (1H, multiplet). Elemental analysis: $C_{22}H_{36}O_5$ Calculated value: C, 69.44% ; H, 9.54% Found: C, 69.52% H, 9.53%.

D. 17-Cyclopentyl-ω-trinor-13,14-dihydro-PGE₁

TLC: Rf = 0.46; NMR spectrum (CDCl₃): δ = 5.69 − 5.08 (3H, broad singlet), 4.30 − 3.97 (1H, multiplet), 3.68 − 3.40 (1H, multiplet), 2.86 − 2.50 (1H, multiplet).
Elemental analysis: $C_{22}H_{38}O_5$
Calculated value: C, 69.07%; H, 10.01%
Found: C, 69.02% ; H, 9.97%.

E. 17-Cyclohexyl-ω-trinor-PGE₂

TLC: Rf = 0.29 NMR spectrum (CDCl₃): δ = 5.74 − 5.54 (2H, multiplet), 5.52 − 5.34 (2H, multiplet), 5.15 − 4.82 (3H, broad singlet), 4.25 − 3.88 (2H, multiplet), 1.87 − 1.58 (1H, multiplet).
Elemental analysis: $C_{23}H_{36}O_5$
Calculated value: C, 70.37% ; H, 9.24%
Found: C, 70.33% ; H, 9.20%.

F. 17-Cyclohexyl-ω-trinor-PGE₁

TLC: Rf = 0.30; NMR spectrum (CDCl₃): δ = 5.65 − 5.49 (2H, multiplet), 5.43 − 5.0 (3H, broad singlet), 2.92 − 2.57 (1H, multiplet).
Elemental analysis: $C_{22}H_{38}O_5$
Calculated value: C, 70.01%; H, 9.71%
Found: C, 69.88%; H, 9.65%.

G. 17-Cyclohexyl-ω-trinor-13,14-dihydro-PGE₁

TLC: Rf = 0.43; NMR spectrum (CDCl₃): δ = 5.75 − 5.13 (3H, broad singlet), 4.28 − 3.96 (1H, multiplet), 3.66 − 3.43 (1H, multiplet), 2.85 − 2.54 (1H, multiplet).
Elemental analysis: $C_{23}H_{40}O_5$
Calculated value : C, 69.66% ; H, 10.17%
Found: C, 69.73% ; H, 10.19%.

For the preparation of starting materials for the aforementioned products refer to Examples 2, 4, and 5.

EXAMPLE 10

16-Cyclohexyl-ω-trinor-PGA₂

42.5 mg. of 16-cyclohexyl-ω-trinor-PGE₂ (prepared as described in Example 8) were dissolved in 3 ml. of a 90 percent aqueous solution of acetic acid and the solution stirred at a temperature of 55°–60°C., for 17 hours. The reaction mixture was then concentrated under reduced pressure and the residue dissolved in diethyl ether. The solution was washed with water; dried and then concentrated under reduced pressure.

The resulting residue was purified by silica gel column chromatography. As eluent a mixture of cyclohexane and ethyl acetate [3:1] was used. The title compound in pure form (a pale yellow oil) was obtained in an amount of 34 mg. TLC (chloroform:tetrahydrofuran:acetic acid = 10:2:1): Rf = 0.81; NMR spectrum (CDCl₃): δ = 7.52 (1H, quartet), 6.2 (1H, quartet), 5.68 − 5.25 (4H, multiplet), 5.12 − 4.50 (2H, broad singlet), 4.30 − 3.92 (1H, multiplet), 3.38 − 3.17 (1H, multiplet), 1.0 − 0.65 (3H, multiplet).
Elemental analysis: $C_{23}H_{34}O_4$
Calculated value: C, 73.76% ; H, 9.15%
Found: C, 73.63% ; H, 9.11%.

The following compounds (A) to (H) were prepared by a similar procedure to that of Example 10. (The developing solvent for TLC was the same as mentioned above in that Example)

A. 16-Cyclohexyl-ω-trinor-PGA₁

TLC: Rf = 0.82; NMR spectrum (CDCl₃): δ = 7.58 − 7.47 (1H, quartet), 6.28 − 5.92 (3H, multiplet), 5.71 − 5.57 (2H, multiplet), 4.28 − 3.98 (1H, multiplet), 3.40 − 3.18 (1H, multiplet), 1.02 −0.65 (3H, multiplet).
Elemental analysis: $C_{23}H_{36}O_4$
Calculated value: C, 73.36% ; H, 9.64%
Found: C, 73.27% ; H, 9.58%.

B. 16-Cyclohexyl-ω-trinor-13,14-dihydro-PGA₁

TLC: Rf = 0.87; NMR spectrum (CDCl₃): δ = 7.71 − 7.56 (1H, quartet), 6.20 − 6.08 (1H, quartet), 4.92 − 4.3 (2H, broad singlet), 3.69 − 3.38 (1H, multiplet), 1.02 − 0.67 (3H, multiplet).
Elemental analysis: $C_{23}H_{38}O_4$
Calculated value: C, 72.97% ; H, 10.12%
Found: C, 73.04% ; H, 10.09%.

C. 17-Cyclohexyl-ω-trinor-PGA₂

TLC: Rf = 0.78; NMR spectrum (CDCl₃): δ = 7.59 − 7.48 (1H, quartet), 6.30 − 5.94 (3H, multiplet), 5.70 − 5.54 (2H, multiplet), 5.54 − 5.34 (2H, multiplet), 4.21 − 3.97 (1H, multiplet), 3.32 − 3.14 (1H, multiplet); IR absorption spectrum (liquid film): 3900, 2950 − 2860, 1740, 1720, 1590 and 1450 cm⁻¹.

D. 17-Cyclohexyl-ω-trinor-PGA₁

TLC: Rf = 0.78; NMR spectrum (CDCl₃): δ = 7.55 − 7.45 (1H, quartet), 6.31 − 6.18 (1H, quartet), 6.08 − 5.84 (2H, broad singlet), 5.74 − 5.52 (2H, multiplet), 4.27 − 4.0 (1H, multiplet), 3.28 − 3.15 (1H, multiplet).
Elemental analysis: $C_{23}H_{36}O_4$
Calculated value: C, 73.36% ; H, 9.64%
Found: C, 73.34% ; H, 9.66%.

E. 17-Cyclohexyl-ω-trinor-13,14-dihydro-PGA₁

TLC: Rf = 0.85; NMR spectrum (CDCl₃): δ = 7.67 − 7.54 (1H, quartet), 6.24 − 6.11 (1H, quartet), 5.42 − 4.95 (2H, broad singlet), 3.65 − 3.39 (1H, multiplet).
Elemental analysis: $C_{23}H_{38}O_4$
Calculated value: C, 72.97% H, 10.12%
Found: C, 72.86% ; H, 10.07%.

F. 17-Cyclopentyl-ω-trinor-PGA₂

TLC: Rf = 0.78; NMR spectrum (CDCl₃): δ = 7.60 − 7.48 (1H, quartet), 6.31 − 6.14 (1H, quartet), 5.89 − 5.54 (4H, quartet), 5.53 − 5.33 (2H, multiplet), 4.27 − 3.99 (1H, multiplet), 3.37 − 3.19 (1H, multiplet).
Elemental analysis: $C_{22}H_{32}O_4$
Calculated value: C, 73.30% ; H, 8.95%

Found: C, 73.27% ; H, 8.87%.

G. 17-Cyclopentyl-ω-trinor-PGA$_1$

TLC: Rf = 0.79; NMR spectrum (CDCl$_3$): δ = 7.56 − 7.45 (1H, quartet), 6.29 − 6.15 (1H, quartet), 5.95 − 5.48 (4H, multiplet), 4.27 − 3.99 (1H, multiplet), 3.33 − 3.16 (1H, multiplet).
Elemental analysis: C$_{22}$H$_{34}$O$_4$
Calculated value: C, 72.89% ; H, 9.45%
Found: C, 72.85% ; H, 9.44%.

H. 17-Cyclopentyl-ω-trinor-13,14-dihydro-PGA$_1$

TLC: Rf = 0.87; NMR spectrum (CDCl$_3$): δ = 7.70 − 7.54 (1H, quartet), 6.21 − 6.08 (1H, quartet), 4.95 − 4.4 (2H, broad singlet), 3.66 − 3.39 (1H, multiplet).
Elemental analysis: C$_{22}$H$_{36}$O$_4$
Calculated value: C, 72.49% ; H, 9.96%
Found: C, 72.54% ; H, 9.98%

For the preparation of starting materials for the aforementioned products refer to Example 9.

REFERENCE EXAMPLE 13

Dimethyl 3-cyclopentyl-2-oxo-butylphosphate 75 g. of dimethyl methylphosphonate were dissolved in 430 ml. of tetrahydrofuran and the solution cooled to −15°C. To the solution there was added drop-wise a solution of butyllithium (prepared from 90 g. of butyl bromide and 8.7 g. of lithium) in 330 ml. of diethyl ether. To the reaction mixture a solution of 31.6 g. of ethyl 2-cyclopentylpropionate in 170 ml. of tetrahydrofuran was added drop-wise, and the mixture stirred at the same temperature for 2 hours and afterwards at 0°C. overnight. The reaction mixture was neutralised with acetic acid, concentrated under reduced pressure and the residue was diluted with water and extracted with diethyl ether. The ethereal layer was dried with sodium sulphate, concentrated under reduced pressure, and distilled in vacuo to obtain 28.5 g. of the title compound as a colourless oil, b.p. 141° − 143°C./0.4 mm.Hg. NMR spectrum (CCl$_4$ solution): δ = 3.83 (6H, doublet), 3.18 (2H, doublet) and 1.12 (3H, doublet).

REFERENCE EXAMPLE 14

2-Oxa-3-oxo-6-syn-(3-oxo-4-cyclopentyl-pent-trans-1-enyl)-7-anti-acetoxy-cis-bicyclo[3,3,0]octane 6.9 g. of sodium hydride (content 64.3%) were suspended in 1.2 litres of dry tetrahydrofuran, and 46 g. of dimethyl 3-cyclopentyl-2-oxo-butylphosphonate (prepared as described in Reference Example 13) in 200 ml. of tetrahydrofuran were added. The reaction mixture was stirred at room temperature for 30 minutes, after which time no further hydrogen was evolved. 49.4 g. of 2-oxa-3-oxo-6-syn-formyl-7-anti-acetoxy-cis-bicyclo[3,3,0]octane [prepared as described in J. Amer. Chem. Soc. 92, 397 (1970)] in 300 ml. of tetrahydrofuran were added to the reaction mixture, which was stirred for two hours at ambient temperature and then neutralised with acetic acid. After concentration under reduced pressure, the residue was chromatographed on silica gel using a mixture of ethyl acetate and benzene (10:90) as eluent to obtain 30.6 g. of the title compound as white crystals, m.p. 90°–93°C. NMR spectrum (CDCl$_3$ solution): δ = 6.75 − 6.62 (1H, doublet), 6.48 (1H, singlet), 5.13 (2H, doublet), 2.04 (3H, singlet) and 1.09 (3H, doublet); IR absorption spectrum (KBr tablet); 1780, 1740, 1680 and 1620 cm$^{-1}$; TLC (benzene:ethyl = 4:1): Rf = 0.56.

REFERENCE EXAMPLE 15

2-Oxa-3-oxo-6-syn-(3-hydroxy-4-cyclopentyl-pent-trans-1-enyl)-7-anti-acetoxy-cis-bicyclo[3,3,0]octane 30.6 g. of 2-oxa-3-oxo-6-syn-(3-oxo-4-cyclopentyl-pent-trans-1-enyl)-7-anti-acetoxy-cis-bicyclo[3,3,-0]octane (prepared as described in Reference Example 14) were dissolved in a mixture of 400 ml. of methanol and 400 ml. of tetrahydrofuran, the solution cooled to −40° to −50°C., and 10.5 g. of sodium borohydride were added in small portions. After stirring for one hour, the reaction mixture was neutralised with oxalic acid at −30°C., allowed to warm to room temperature and concentrated. The residue was mixed with water and ethyl acetate, washed with water and saturated aqueous sodium bicarbonate solution, dried and concentrated. The residue was subjected to silica gel column chromatography using a mixture of diethyl ether, n-hexane and ethyl acetate (5:3:2) as eluent, and 26.8 g. of the title compound were obtained as a colourless oil. NMR spectrum (CDCl$_3$ solution): δ = 5.7 − 5.5 (2H, multiplet), 5.2 − 4.8 (2H, multiplet), 4.2 (1H, singlet) and 1.0 − 0.7 (3H, doublet); IR absorption spectrum (liquid film): 3500, 2950, 2910, 2860, 1770, 1740 and 975 cm$^{-1}$; TLC (benzene:ethyl acetate = 2:3): Rf = 0.58.

REFERENCE EXAMPLE 16

2-Oxa-3-hydroxy-6-syn-[3-(2-tetrahydropyranyloxy)-4-cyclopentyl-pent-trans-1-enyl]-7-anti-(2-tetrahydropyranyloxy)-cis-bicyclo[3,3,0]octane A methanolic solution of 6.5 g. of 2-oxa-3-oxo-6-syn-(3-hydroxy-4-cyclopentyl-pent-trans-1-enyl)-7-anti-acetoxy-cis-bicyclo[3,3,0]octane (prepared as described in Reference Example 15) was hydrolysed with an equimolar amount of potassium carbonate at 25°C. to obtain 5.5 g. of 2-oxa-3-oxo-6-syn-(3-hydroxy-4-cyclopentyl-pent-trans-1-enyl)-7-anti-hydroxy-cis-bicyclo[3,3,0]octane.

A methylene chloride solution of 5.6 g. of the dihydroxy compound thus obtained was reacted with 10 equimolar amounts of dihydropyran and a small amount of p-toluenesulphonic acid as catalyst at 25°C. for 15 minutes to yield 8.9 g. of 2-oxa-3-oxo-6-syn-[3-(2-tetrahydropyranyloxy)-4-cyclopentyl-pent-trans-1-enyl]-7-anti-(2-tetrahydropyranyloxy)-cis-bicyclo[3,3,0]octane.

8.6 g. of the said bis-tetrahydropyranyl compound in toluene were reduced with 2 equimolar amounts of diisobutylaluminium hydride at −60°C. for 30 minutes to yield 8.6 g. of the title compound.

EXAMPLE 11

9α-Hydroxy-11α,15-di-(2-tetrahydropyranyloxy)-16-cyclopentyl-ω-trinor-prosta-cis-5, trans-13-dienoic acid A solution of 31 g. (0.14 mole) of 4-carboxy-n-butyl-triphenylphosphonium bromide in 50 ml. of dimethylsulphoxide was mixed with 70 ml. of dimethylsulphoxide containing 2 molecular equivalents of sodiomethylsulphinylcarbanide (0.14 mole as sodiomethylsulphinylcarbanide) whilst maintaining the temperature at 25°C. To the resulting red mixture was added a solution containing 13 g. of 2-oxa-3-hydroxy-6-syn-[3-(2-tetrahydropyranyloxy)-4-cyclopentyl-pent-trans-1-enyl]-7-anti-(2-tetrahydropyranyloxy)-cis-bicyclo[3,3,0]- octane (prepared as described in Reference Example 16) in 50 ml. of dimethylsulphoxide. The reaction mixture was stirred for 1 hour at 25°C., poured into 850 ml. of ice-water containing a small amount of potassium carbonate, and then extracted with a mixture of diethyl ether and ethyl acetate (1:1) to remove the neutral substances. The aqueous layer was then adjusted to pH 2 with oxalic acid and extracted four times with a mixture of diethyl ether and n-pentane (1:1); the organic layer after separation was washed with water, dried and concentrated under reduced pressure. The residue was purified by silica gel column chromatography using an ethanol-benzene mixture (1:20) as eluent to give 8.4 g. of the title compound as a colourless oil. NMR spectrum (CDCl$_3$ solution): $\delta = 6.5$ (2H, broad singlet), 5.2 − 5.7 (4H, multiplet), and 4.80 (2H, multiplet); IR absorption spectrum (liquid film): 3450, 2930, 2860, 2800 − 2400, 1725, 1710, 1120, 1080, 1035, 1025 and 980 cm$^{-1}$; TLC (benzene:ethyl acetate = 1:1): Rf = 0.27.

EXAMPLE 12

9α-Hydroxy-11α,15-di-(2-tetrahydropyranyloxy)-16-cyclopentyl-ω-trinor-prost-trans-13-enoic acid 700 mg. of 5% palladium on carbon were suspended in 20 ml. of methanol. Air in the apparatus was replaced with hydrogen and a solution of 2.1 g. of 9α-hydroxy-11α,15-di-(2-tetrahydropyranyloxy)-16-cyclopentyl-ω-trinor-prosta-cis-5, trans-13-dienoic acid (prepared as described in Example 11) in 40 ml. of methanol was added thereto. Catalytic reduction of the compound was carried out at room temperature under ambient pressure for about 30 minutes. After completion of the reaction, the catalyst was filtered off and the filtrate was condensed to dryness under reduced pressure. The yield of the title compound was 1.4 g. IR absorption spectrum (liquid film): 3430, 2940, 2860, 2700 − 2350, 1710, 1445, 1380, 1260, 1200 and 1025 cm$^{-1}$.

EXAMPLE 13

9α-Hydroxy-11α,15-di-(2-tetrahydropyranyloxy)-16-cyclopentyl-ω-trinor-prostanoic acid 1.05 g. of 9α-hydroxy-11α,15-di-(2-tetrahydropyranyloxy)-16-cyclopentyl-ω-trinor-prosta-cis-5, trans-13-dienoic acid (prepared as described in Example 11) in 12 ml. of ethanol were subjected to catalytic hydrogenation in the presence of 100 mg. of platinum oxide at ambient temperature under an atmospheric pressure. After the completion of the reaction, the catalyst was filtered off and the filtrate was condensed to dryness under reduced pressure to give 860 mg. of the title compound.

EXAMPLE 14

16-Cyclopentyl-ω-trinor-PGF$_{2\alpha}$ and 16-cyclopentyl-ω-trinor-15-epi-PGF$_{2\alpha}$ 1.0 g. of 9α-hydroxy-11α, 15-di-(2-tetrahydropyranyloxy)-16-cyclopentyl-ω-trinor-prosta-cis-5, trans-13-dienoic acid (prepared as described in Example 11) was dissolved in a mixture of 7.85 ml. of tetrahydrofuran, 0.915 ml. of hydrochloric acid and 6.95 ml. of water and the solution stirred vigorously at 35°C. for 1.5 hours. The reaction mixture was poured into 150 ml. of ice-water and extracted with ethyl acetate. The organic layer was washed with water, dried with magnesium sulphate and concentrated under reduced pressure. The residue was subjected to silica gel column chromatography using a cyclohexane-ethyl acetate mixture (1:1) as eluent to obtain 226 mg. of 16-cyclohexyl-ω-trinor-PGF$_{2\alpha}$ and 192 mg. of 16-cyclohexyl-ω-trinor-15-epi-PGF$_{2\alpha}$. NMR spectrum (CDCl$_3$ solution): $\delta = 5.64 - 5.30$ (4H, multiplet), 4.3 − 3.5 (7H, multiplet and broad singlet) and 1.0 − 0.8 (3H, doublet); IR absorption spectrum (liquid film): 3400, 2950, 2910, 2850, 2800 − 2300, 1720 and 980 cm$^{-1}$; TLC (chloroform:tetrahydrofuran:acetic acid = 10:2:1):16-cyclopentyl-ω-trinor-PGF$_{2\alpha}$ : Rf = 0.12 16-cyclopentyl-ω-trinor-15-epi-PGF$_{2\alpha}$ : Rf = 0.33.

EXAMPLE 15

16-Cyclopentyl-ω-trinor-PGF$_{1\alpha}$ and 16-cyclopentyl-ω-trinor-15-epi-PGF$_{1\alpha}$ 630 mg. of 9α-hydroxy-11α,15-di-(2-tetrahydropyranyloxy)-16-cyclopentyl-ω-trinor-prost-trans-13-enoic acid (prepared as described in Example 12) were dissolved in a mixture of 5 ml. of tetrahydrofuran, 4.4 ml. of water and 0.8 ml. of 12N hydrochloric acid, and the mixture was stirred at room temperature for one hour. Manner of post-treatment of the reaction mixture and purification of the product was the same as in Example 14. Yields of 16-cyclopentyl-ω-trinor-PGF$_{1\alpha}$ and 16-cyclopentyl-ω-trinor-15-epi-PGF$_{1\alpha}$ were 144 mg. and 130 mg. respectively. NMR spectrum (CDCl$_3$ solution): $\delta = 5.76 - 5.52$ (2H, multiplet), 5.30 − 4.75 (4H, broad singlet), 4.24 − 3.80 (3H, multiplet) and 1.03 − 0.75 (3H, doublet); IR absorption spectrum (liquid film); 3350, 2950, 2860, 2800 − 2300, 1705, 1460 and 1020 cm$^{-1}$; TLC (chloroform:tetrahydrofuran:acetic acid = 10:2:1): 16-cyclopentyl-ω-trinor-PGF$_{1\alpha}$ : Rf = 0.13  16-cyclopentyl-ω-trinor-15-epi-PGF$_{1\alpha}$ : Rf = 0.29.

EXAMPLE 16

16-Cyclopentyl-ω-trinor-13,14-dihydro-PGF$_1\alpha$ 405 mg. of 9α-hydroxy-11α, 15-di-(2-tetrahydropyranyloxy)-16-cyclopentyl-ω-trinor-prostanoic acid (prepared as described in Example 13) were dissolved in a mixture of 3 ml. of tetrahydrofuran, 2.7 ml. of water and 0.5 ml. of 12N hydrochloric acid, and the solution was stirred at room temperature for 1 hour. Manner of post-treatment of the reaction mixture and purification of the product was the same as in Example 14, but 16-cyclopentyl-ω-trinor-15-epi-13,14-dihydro-PGF$_1$ could not be separated from 16-cyclopentyl-ω-trinor-13,14-dihydro-PGF$_1$ . Therefore, the product was a mixture of 15α- and 15β-hydroxy compounds. Yield was 160 mg. NMR spectrum (CDCl$_3$ solution): $\delta = 4.85 - 4.46$ (4H, broad singlet), 4.26 − 4.05 (1H, multiplet), 4.05 − 3.84 (1H, multiplet), 3.65 − 3.37 (1H, multiplet) and 1.0 − 0.75 (3H, doublet).

EXAMPLE 17

16-Cyclopentyl-ω-trinor-PGE$_2$ and 16-cyclopentyl-ω-trinor-15-epi-PGE$_2$ 2.0 g. of 9α-hydroxy-11α, 15-di-(2-tetrahydropyranyloxy)-16-cyclopentyl-ω-trinor-prosta-cis-5, trans-13-dienoic acid (prepared as described in Example 11) were dissolved in 68 ml. of diethyl ether, and the solution cooled to 0° − 5°C. Then 63 ml. of a chromic acid solution (prepared by dissolving 3.2 g. of chromium trioxide, 10.8 g. of manganese sulphate and 3.56 ml. of sulphuric acid in water to make the total volume 80 ml.) were added to the solution. The reaction mixture was stirred vigorously at 0° – 5°C. for one hour and then diluted with diethyl ether to separate it into layers. The aqueous layer after separation was extracted with diethyl ether. The combined extracts were washed with sufficient water until the washing was not coloured yellow, dried over sodium sulphate and then concentrated under reduced pressure. The residue was subjected to silica gel column chromatography using a benzene-ethyl acetate mixture (3:2) as eluent to obtain 1.9 g. of 9-oxo-11α, 15-di-(2-tetrahydropyranyloxy)-16-cyclopentyl-ω-trinor-prosta-cis-5, trans-13-dienoic acid as an oil. IR absorption spectrum (liquid film): 3400 – 3100, 2950, 2860, 2800 – 2400, 1740, 1710, 1120, 1080, 1035, 1025 and 980 cm$^{-1}$; TLC (benzene:ethyl acetate = 1:1): Rf = 0.38.

1.9 g. of the said oxo compound were dissolved in a mixture of 2.58 ml. of tetrahydrofuran, 16.7 ml. of acetic acid and 9.1 ml. of water and the solution stirred at 38° to 42°C. for 4.5 hours. The reaction mixture was then poured into 250 ml. of ice-water, extracted with ethyl acetate, washed with water, dried over sodium sulphate and concentrated under reduced pressure. The residue was subjected to silica gel chromatography using a cyclohexane-ethyl acetate mixture (1:1) as eluent to obtain 494 mg. of 16-cyclopentyl-ω-trinor-PGE$_2$ and 400 mg. of 16-cyclopentyl-ω-trinor-15-epi-PGE$_2$. NMR spectrum (CDCl$_3$ solution): δ = 5.74 – 5.5 (2H, multiplet), 5.5 – 5.1 (5H, multiplet and broad singlet), 4.23 – 3.9 (2H, multiplet), 2.9 – 2.6 (1H, doublet-doublet) and 1.0 – 0.8 (3H, doublet); IR absorption spectrum (liquid film): 3370, 2930, 2850, 2800 – 2300, 1730, 1710 and 980 cm$^{-1}$; TLC (chloroform:tetrahydrofuran:acetic acid = 10:2:1): 16-cyclopentyl-ω-trinor-PGE$_1$: Rf = 0.19 16-cyclopentyl-ω-trinor-15-epi-PGE$_1$: Rf = 0.33.

EXAMPLE 18

16-Cyclopentyl-ω-trinor-PGE$_1$ and 16-cyclopentyl-ω-trinor-15-epi-PGE$_1$ 2.0 g. of 9α-hydroxy-11α,15-di-(2-tetrahydropyranyloxy)-16-cyclopentyl-ω-trinor-prost-trans-13-enoic acid (prepared as described in Example 12) were dissolved in 70 ml. of diethyl ether and the solution was stirred vigorously together with 63 ml. of a chromic acid solution (having the same composition as in Example 17) at 0°– 5°C. for two hours. The reaction mixture was subjected to the same post-treatment as described in Example 17 to obtain 9-oxo-11α,15-di-(2-tetrahydropyranyloxy)-16-cyclopentyl-ω-trinor-prost-trans-13-enoic acid.

The oxo compound was dissolved in 21 ml. of a mixture of acetic acid, water and tetrahydrofuran (65:35:10), and the solution stirred at 38°C. The hydrolysate was subjected to an after-treatment and purification by column chromatography similar to that described in Example 17 to give 336 mg. of 16-cyclopentyl-ω-trinor-PGE$_1$ and 344 mg. of 16-cyclopentyl-ω-trinor-15-epi-PGE$_1$. NMR spectrum (CDCl$_3$ solution): δ– 5.7 – 5.5 (2H, multiplet), 5.5 – 5.0 (3H, broad singlet), 4.3 – 3.9 (2H, multiplelt), 2.9 – 2.6 (1H, doublet-doublet) and 0.9 – 0.8 (3H, doublet); IR absorption spectrum (liquid film): 3400, 2950, 2850, 2700 – 2300, 1735, 1710 and 975 cm$^{-1}$; TLC (chloroform:tetrahydrofuran:acetic acid = 10:2:1): 16-cyclopentyl-ω-trinor-PGE$_1$: Rf = 0.15 16-cyclopentyl-ω-trinor-15-epi-PGE$_1$: Rf = 0.29.

EXAMPLE 19

16-Cyclopentyl-ω-trinor-13, 14-dihydro-PGE$_1$ 820 mg. of 9α-hydroxy-11α, 15-di-(2-tetrahydropyranyloxy)-16-cyclopentyl-ω-trinor-prostanoic acid (prepared as described in Example 13) were dissolved in 30 ml. of diethyl ether and the solution was stirred vigorously together with 25 ml. of a chromic acid solution (having the same composition as in Example 17) at 0°– 5°C., for 1.5 hours. The reaction mixture was subjected to the same post-treatment as described in Example 17 to obtain 9-oxo-11α, 15-di-(2-tetrahydropyranyloxy)-16-cyclopentyl-ω-trinor-prostanoic acid.

The resulting oxo compound was dissolved in 10 ml. of a mixture of acetic acid, water and tetrahydrofuran (65:35:10), and the solution stirred at 38°C. The hydrolysate was subjected to an after-treatment and purification by column chromatography similar to that described in Example 17 to give 265 mg. of 16-cyclopentyl-ω-trinor-13, 14-dihydro-PGE$_1$. The product was a mixture of 15α- and 15β-hydroxy compounds. NMR spectrum (CDCl$_3$ solution): δ = 5.60 – 5.10 (3H, broad singlet), 4.30 – 3.99 (1H, multiplet), 3.66 – 3.40 (1H, multiplet), 2.86 – 2.56 (1H, doublet-doublet) and 0.95 – 0.77 (3H, doublet).

EXAMPLE 20

16-Cyclopentyl-ω-trinor-PGA$_2$ 177 mg. of 16-cyclopentyl-ω-trinor-PGE$_2$ (prepared as described in Example 17) were dissolved in 34 ml. of a mixture of tetrahydrofuran and 1N hydrochloric acid (1:1); 80 mg. of cupric chloride dihydrate were added and the mixture stirred at 60°C. for 2 hours. The reaction mixture was then diluted with ethyl acetate, washed with water, dried over magnesium sulphate and concentrated under reduced pressure. The residue was subjected to silica gel column chromatography using cyclohexane-ethyl acetate (3:1) as eluent to give 113 mg. of the title compound as an oil. NMR spectrum (CDCl$_3$ solution): δ= 7.55 – 7.45 (1H, doublet-doublet), 6.23 – 6.13 (1H, doublet-doublet), 5.75 (2H, broad singlet), 5.7 – 5.55 (2H, multiplet), 3.39 – 3.16 (1H, multiplet) and 0.95 – 0.8 (3H, doublet); IR absorption spectrum (liquid film): 3350, 2950, 2860, 2800 – 2200, 1710, 1585 and 980 cm$^{-1}$; TLC (chloroform:tetrahydrofuran:acetic acid = 10:2:1): Rf = 0.64.

EXAMPLE 21

16-Cyclopentyl-ω-trinor-PGA$_1$ 100 mg. of 16-cyclopentyl-ω-trinor-PGE$_1$ (prepared as described in Example 18) were dissolved in 20 ml. of a mixture of tetrahydrofuran and 1N hydrochloric acid (1:1); 48 mg. of cupric chloride dihydrate were added and the mixture stirred at 57°– 60°C. for 2 hours. The reaction product was subjected to an after-treatment and purification by column chromatography similar to that described in Example 20 to obtain 69 mg. of 16-cyclopentyl-ω-trinor-PGA$_1$ as a colourless oil. NMR spectrum (CDCl$_3$ solution): δ = 7.56 – 7.45 (1H, doublet-doublet), 6.23 – 6.13 (1H, doublet-doublet), 5.73 – 5.23 (4H, multiplet and broad singlet), 4.30 – 3.93 (1H, multiplet), 3,39 – 3.18 (1H, multiplet) and 0.98 – 0.8 (3H, doublet); IR absorption spectrum (liquid film): 3360, 2950, 2860, 2800 −2300, 1705 and 1585 cm$^{-1}$; TLC (chloroform: tetrahydrofuran: acetic acid = 10:2:1): Rf = 0.65.

EXAMPLE 22

16-Cyclopentyl-ω-trinor-13, 14-dihydro-PGA$_1$ 138 mg. of 16-cyclopentyl-ω-trinor-13, 14-dihydro-PGE$_1$ (prepared as described in Example 19) were dissolved in 27 ml. of a mixture of tetrahydrofuran and 1N hhydrochloric acid (1:1); 57 mg. of cupric chloride dihydrate were added and the mixture stirred at 60°C., for 2.5 hours. The reaction mixture was subjected to a post-treatment and purification by column chromatography similar to that described in Example 20 to obtain 85 mg. of 16-cyclopentyl-ω-trinor-13, 14-dihydro-PGA$_1$ as a colourless oil. NMR spectrum (CDCl$_3$ solution): δ = 7.71 − 7.56 (1H, doublet-doublet), 6.22 − 6.10 (1H, doublet-doublet), 5.2 − 4.7 broad singlet), 3.73 − 3.38 (1H, multiplet), and 0.97 − 0.78 (3H, doublet).

EXAMPLE 23

16-Cyclohexyl-ω-trinor-PGE$_1$ methyl ester

A newly prepared ethereal solution of diazomethane was added to 27 mg. of 16-cyclohexyl-ω-trinor-PGE$_1$ (prepared as described in Example 9) until a light yellow colour did not vanish. After stirring at 0°C., for ten minutes, the excess of diazomethane was decomposed with a dilute ethereal solution of acetic acid, and the reaction mixture was concentrated under reduced pressure. The residue was purified by column chromatography on silica gel using an ethyl acetate-cyclohexane mixture (1:1) as eluent to give 18 mg. of pure 16-cyclohexyl-ω-trinor-PGE$_1$ methyl ester as a colourless oil. NMR spectrum (CDCl$_3$ solution): δ = 5.8 − 5.4 (2H, multiplet), 4.3 − 3.8 (2H, multiplet), 3,68 (3H, singlet), 2.95 − 2.55 (1H, doublet-doublet) and 0.9 − 0.65 (3H, doublet); IR absorption spectrum (CHCl$_3$ solution): 3430, 2980, 2950, 2880, 2870, 1735 and 975 cm$^{-1}$; TLC (chloroform:tetrahydrofuran:acetic acid = 10:2:1): Rf = 0.53.

EXAMPLE 24

16-Cyclohexyl-ω-trinor-PGE$_1$ isobutyl ester

From 27 mg. of 16-cyclohexyl-ω-trinor-PGE$_1$ and a freshly prepared ethereal solution of diazoisobutane, there was obtained 20 mg. of the corresponding isobutyl ester as an oil. NMR spectrum (CDCl$_3$ solution): δ = 5.7 − 5.5 (2H, multiplet), 4.3 − 3.8 (2H, multiplet), 3.93 − 3.78 (2H, doublet), 295 − 2.55 (1H, doublet-doublet) and 0.9 − 0.65 (3H, doublet); IR absorption spectrum (CHCl$_3$ solution): 3450, 2980, 2945, 2880, 2870, 1735 and 980 cm$^{-1}$; TLC (chloroform:tetrahydrofuran:acetic acid = 10:2:1): Rf = 0.54.

EXAMPLE 25

16-Cyclohexyl-ω-trinor-PGE$_1$ decyl ester

From 50 mg. of 16-cyclohexyl-ω-trinor-PGE$_1$ and a freshly prepared ethereal solution of diazodecane, there was obtained 44 mg. of the corresponding decyl ester as an oil. NMR spectrum (CDCl$_3$ solution): δ = 5.75 − 5.4 (2H, multiplet), 4.3 − 3.8 (2H, multiplet), 2.95 − 2.55 (1H, doublet-doublet) and 1.0 − 0.85 (6H, multiplet); IR absorption spectrum (CHCl$_3$ solution): 3450, 2980, 2950, 2880, 2870, 1735 and 980 cm$^{-1}$; TLC (chloroform:tetrahydrofuran:acetic acid = 10:2:1): Rf = 0.60.

The present invention includes within its scope pharmaceutical compositions which comprise at least one new therapeutically useful prostaglandin compound according to the present invention, together with a pharmaceutical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.01 and 5 mg/kg. body weight by oral administration in the treatment of hypertension, between 0.5 and 100 μ/kg. body weight by oral administration in the treatment of gastric ulceration, between 0.1 and 50 μ/kg. body weight by aerosol administration in the treatment of asthma, between 0.01 and 5 mg./kg. body weight by oral administration in the treatment of disorders of the peripheral circulation and between 0.01 and 5 mg./kg. body weight by oral administration in the prevention and treatment of cerebral thrombosis and myocardial infarction; between 0.1 and 10 milligrams per body by intrauterine administration in the control of oestrus and in the prevention of pregnancy, and between 0.1 and 10 milligrams per body by intravenous infusion in the induction of labour.

Prostaglandin compounds according to the present invention may be administered orally as bronchodilators by any method known per se for administration by inhalation of drugs which are not themselves gaseous normal conditions of administration. Thus, a solution of the active ingredient in a suitable pharmaceutically-acceptable solvent, for example water, can be nebulized by a mechanical nebulizer, for example a Wright Nebulizer, to give an aerosol of finely divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely divided form, preferably micronized to an average particle size of less than 5 microns, the active ingredients in pharmaceutically acceptable solvents, e.g. ehtanol, which are co-solvents assisting in dissolving the active ingredients in the volatile liquid propellants hereinafter described, or pharmaceutically acceptable suspending or dispersing agents, for example aliphatic alcohols such as oleyl alcohol, and incorporating the solutions or suspensions obtained with pharmaceutically acceptable volatile liquid propellants, in conventional pressurized packs which may be made of any suitable material, e.g. metal, plastics or glass, adequate to withstand the pressures generated by the volatile propellant in the pack. Pressurized pharmaceutically acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include flourochlorinated alkanes containing from one to four, and preferably one or two, carbon atoms, for example dichlorodifloromethane, dichlorotetraflouroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C,) and dichlorotetrafluoroethane (vapour pressure 28 pounds per square inch gauge at 21°C,) may be mixed in varying proportions to give propellants having vapour pressures intermediate between those of two constituents, e.g. a mixture of dichlorodifluoromethane and dichlorotetrafluoroethane in the proportions 38:62 respectively, by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredient per ml. of solution or suspension. It is important that the pH of solutions and suspensions used, according to the present invention, to generate aerosols should be kept within the range 3 to 8 and preferable that they should be stored at or below 4°C., to avoid pharmacological deactivation of the active ingredient.

In carrying out the present invention, the means of producing an aerosol for inhalation should be selected in accordance with the physico-chemical properties of the active ingredient.

By the term "pharmaceutically acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is be means of devices enabling controlled quantities of the active ingredients to be administered, for example by means of the metered valves hereinbefore mentioned.

The following Examples illustrates pharmaceutical compositions according to the invention.

EXAMPLE 26

16-Cyclohexyl-ω-trinor-PGE$_2$ (500 μg.) was dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 50 μg. of 16-cyclohexyl-μ-trinor-PGE$_2$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 27

16-Cyclohexyl-μ-trinor-PGE$_2$ (20 mg.) was dissolved in ethanol (10 ml.), mixed with mannitol (18.5 g.), sieved through a 30-mesh sieve, dried at 30°C. for 90 minutes and again sieved through a 30-mesh sieve. Aerosil (microfine silica; 200 mg.) was added and the powder obtained was machine-filled into one hundred No. 2 hard gelatin capsules to give capsules each containing 200 μg. of 16-cyclohexyl-ω-trinor-PGE$_2$, which after swallowing of the capsules is released into the stomach.

What we claim is:
1. A compound of the formula:

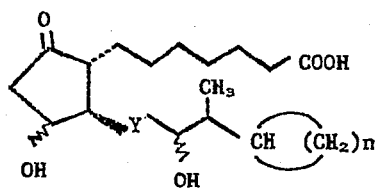

wherein Y represents trans—CH=CH— or CH$_2$CH$_2$—, n represents 4 or 5, and $\sim$ indicates attachment of the hydroxy radical to the carbon atom in alpha or beta configuration, and alkyl esters thereof having from 1 to 12 carbon atoms in a straight- or branched-chain, and cyclodextrin clathrates of such acids and esters, and non-toxic salts of such acids.

2. A compound according to claim 1 which is 16-Cyclohexyl-ω-trinor-PGE$_1$.

3. A compound according to claim 1 which is 16-Cyclohexyl-ω-trinor-13,14-dihydro-PGE$_1$.

4. A compound according to claim 1 which is 16-Cyclopentyl-ω-trinor-PGE$_1$.

5. A compound according to claim 1 which is 16-Cyclopentyl-ω-trinor-15-epi-PGE$_1$.

6. A compound according to claim 1 which is 16-Cyclopentyl-ω-trinor-13,14-dihydro-PGE$_1$.

7. A compound according to claim 1 which is 16-Cyclohexyl-ω-trinor-PGE$_1$ methyl ester.

8. A compound according to claim 1 which is 16-Cyclohexyl-ω-trinor-PGE$_1$ isobutyl ester.

9. A compound according to claim 1 which is 16-Cyclohexyl-ω-trinor-PGE$_1$ decyl ester.

* * * * *